(12) United States Patent
Busch et al.

(10) Patent No.: US 6,673,929 B2
(45) Date of Patent: Jan. 6, 2004

(54) PROCESS FOR PREPARING GROWTH HORMONE SECRETAGOGUES

(75) Inventors: Frank R. Busch, Gales Ferry, CT (US);
Charles K. Chiu, Guilford, CT (US);
Clifford N. Meltz, Niantic, CT (US);
Ronald J. Post, Mystic, CT (US);
Peter R. Rose, Ledyard, CT (US)

(73) Assignee: Pfizer Inc., New York, NY (US)

( * ) Notice: Subject to any disclaimer, the term of this patent is extended or adjusted under 35 U.S.C. 154(b) by 12 days.

(21) Appl. No.: 10/283,720

(22) Filed: Oct. 30, 2002

(65) Prior Publication Data

US 2003/0158414 A1 Aug. 21, 2003

Related U.S. Application Data

(62) Division of application No. 09/496,075, filed on Feb. 1, 2000, now Pat. No. 6,541,634.
(60) Provisional application No. 60/122,745, filed on Feb. 26, 1999.

(51) Int. Cl.[7] ............................................. C07D 471/04
(52) U.S. Cl. ...................................... 546/120; 546/119
(58) Field of Search .................................. 546/120, 119

(56) References Cited

U.S. PATENT DOCUMENTS

| 4,975,435 A | 12/1990 | Campbell et al. | ........... 514/292 |
| 4,985,444 A | 1/1991 | Shiokawa et al. | ........... 514/300 |

FOREIGN PATENT DOCUMENTS

| RU | 95113347 | 9/1995 | ............ C07K/5/02 |
| RU | 96115171 | 7/1996 | ............ C07K/5/107 |
| WO | WO 9513069 | 5/1995 | ......... A61K/31/445 |
| WO | WO 9632979 | 10/1996 | .......... A61M/15/00 |
| WO | WO 9724369 | 7/1997 | ............. C07K/5/06 |
| WO | WO 9734604 | 9/1997 | .......... A61K/31/445 |
| WO | WO 9736873 | 10/1997 | .......... C07D/221/20 |
| WO | WO 9858947 | 12/1998 | ........... C07K/5/023 |
| WO | WO 9858948 | 12/1998 | ........... C07K/5/023 |
| WO | WO 9858949 | 12/1998 | ............. C07K/5/06 |

OTHER PUBLICATIONS

US 4,385,051, 5/1983, Oka et al. (withdrawn)
Abstract of Russian Patent 96115171 with English Translation of relevant parts.

*Primary Examiner*—Amelia Owens
(74) *Attorney, Agent, or Firm*—Peter C. Richardson; Gregg C. Benson; John A. Wichtowski

(57) ABSTRACT

This invention relates to improved processes for preparing compounds of Formula II,

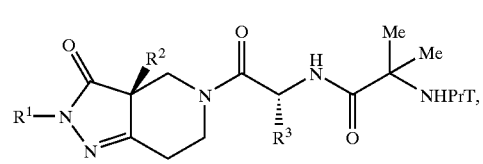

and compounds of Formula III,

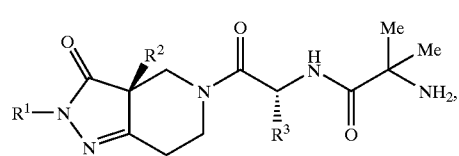

wherein $R^1$, $R^2$, $R^3$ and Prt are defined as set forth in the specification.

53 Claims, 1 Drawing Sheet

PROCESS FOR PREPARING GROWTH HORMONE SECRETAGOGUES

CROSS REFERENCE TO RELATED APPLICATIONS

This is a divisional application of U.S. Ser. No. 09/496,075, filed Feb. 1, 2000, now U.S. Pat. No. 6,541,634 B1 which claims the benefit of U.S. Provisional Application No. 60/122,745, filed Feb. 26, 1999.

BACKGROUND OF THE INVENTION

This invention relates to an improved process for preparing compounds of Formula II comprising coupling a compound of Formula IV with a compound of Formula V. This invention also relates to an improved process for preparing compounds of Formula III by coupling a compound of Formula IV with a compound of Formula V and subsequent deprotection of the resulting Prt-protected compound of Formula II.

Commonly assigned International Patent Application Publication No. WO97/24369, hereinafter referred to as the '369 application, which is incorporated herein by reference, discloses certain growth hormone secretagogue compounds of Formula I,

I wherein the definitions of the variables are disclosed therein. Said compounds are disclosed in the '369 application to have utility in treating, inter alia, osteoporosis.

Compounds of Formula II,

II are disclosed in the '369 application as intermediates in a process to prepare the compounds of Formula III,

III which are within the scope of the disclosure of said international application.

The process disclosed in the '369 application requires coupling a compound of Formula IV with a compound of Formula V. The first step in the coupling reaction is the reaction of a compound of Formula IV below with an organic amine to form the free base of the compound of Formula IV and the organic amine salt of tartaric acid. The next step in the disclosed process is a filtration step to remove the organic amine salt of tartaric acid. This was thought to be necessary to eliminate the possibility of reaction of tartaric acid with the compound of Formula IV under the coupling conditions. Due to the racemization of the 3a position of the pyrazolo[4,3-c]pyridine which occurs at room temperature, this filtration had to be performed cryogenically, i.e., at reduced temperatures. When operating the coupling reaction on a bulk scale, cryogenic filtration presents technical problems, e.g., entrainment, slow filtration, a need to use additional equipment and extra handling. This results in reduced yields of product. In the process of this invention, the cryogenic filtration is avoided, resulting in a more streamlined process and an improved chemical and optical yield.

SUMMARY OF THE INVENTION

This invention is directed to a process, designated Process A, of preparing a compound of Formula II,

II wherein:

$R^1$ is —($C_1$–$C_{10}$)alkyl optionally substituted with up to three fluoro atoms;

$R^2$ is phenylmethyl or 2-pyridylmethyl;

$R^3$ is —($C_1$–$C_5$)alkyl-O—($C_0$–$C_5$)alkylphenyl, where the phenyl substituent in the definition of $R^3$ is optionally substituted with up to three fluoro atoms; and Prt is an amine protecting group, comprising:

a) mixing an appropriate chiral tartrate salt having the structure of Formula IV,

IV

D- or L-tartaric acid wherein $R^1$ and $R^2$ are as defined above,
and an organic amine in a reaction inert solvent at a temperature of about −68° C. to about −40° C. to form a slurry;

b) adding a compound of the Formula V,

V wherein R³ and Prt are as defined above, to said slurry to form a reaction mixture comprising the tartrate salt of the organic amine, the free base of a compound of Formula IV and a compound of the formula V; and c) adding a coupling reagent to said reaction mixture to form a compound of Formula II.

A preferred process within Process A, designated Process B, is a process wherein said compound of Formula IV is suspended in said solvent prior to the addition of said organic amine.

A preferred process within Process B, designated Process C, is a process wherein said slurry is warmed to about −50° C. prior to step b.

Another preferred process within Process A, designated Process D, is the process wherein: in step a, said organic amine is triethylamine; in step b, R³ is phenylmethyloxymethyl or 2,4-difluorophenylmethyloxymethyl and Prt is t-butyloxycarbonyl; and in step c, said coupling reagent is propane phosphonic acid anhydride.

A preferred process of Process D, designated Process E, is a process wherein R¹ is methyl or 2,2,2-trifluoroethyl and R² is phenylmethyl or 2-pyridylmethyl.

A preferred process of Process E is a process wherein the compound of Formula II selected from (1-(2-(1(R)-(2,4-difluorobenzyloxymethyl)-3a(R)-pyridin-2-ylmethyl-2-(2,2,2-trifluoro-ethyl)-3-oxo-2,3,3a,4,6,7-hexahydro-pyrazolo[4,3-c]pyridin-5-yl)-2-oxo-ethylcarbamoyl)-1-methyl-ethyl)-carbamic acid tert-butyl ester and (1-(2-(3a(R)-benzyl-2-methyl-3-oxo-2,3,3a,4,6,7-hexahydro-pyrazolo[4,3-c]pyridin-5-yl)-1(R)-benzyloxymethyl-2-oxo-ethylcarbamoyl)-1-methyl-ethyl)-carbamic acid tert-butyl ester is prepared.

Another preferred process of Process E is a process wherein a compound of Formula IIA,

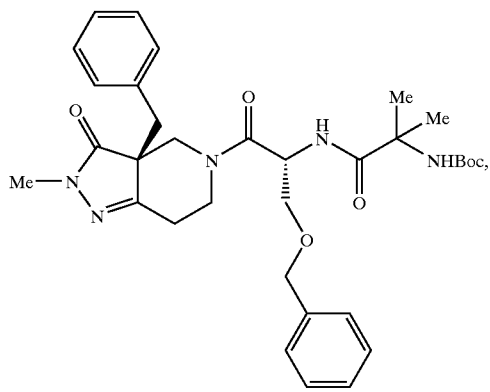

IIA is prepared.

Another preferred process of Process E is the process wherein a compound of Formula IIB,

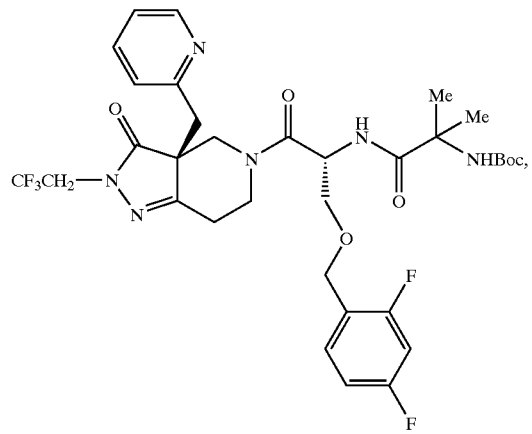

IIB is prepared.

Another preferred process within Process B, designated Process F, is the process wherein: in step a, said organic amine is triethylamine; in step b, R³ is phenylmethyloxymethyl or 2,4-difluorophenylmethyloxymethyl and Prt is t-butyloxycarbonyl; and in step c, said coupling reagent is propane phosphonic acid anhydride.

A preferred process within Process F, designated Process G, is a process wherein R¹ is methyl or 2,2,2-trifluoroethyl and R² is phenylmethyl or 2-pyridylmethyl.

A preferred process within Process F is a process wherein the compound of Formula II selected from (1-(2-(1(R)-(2,4-difluorobenzyloxymethyl)-3a(R)-pyridin-2-ylmethyl-2-(2,2,2-trifluoro-ethyl)-3-oxo-2,3,3a ,4,6,7-hexahydro-pyrazolo[4,3-c]pyridin-5-yl)-2-oxo-ethylcarbamoyl)-1-methyl-ethyl)-carbamic acid tert-butyl ester and (1-(2-(3a(R)-benzyl-2-methyl-3-oxo-2,3,3a,4,6,7-hexahydro-pyrazolo[4,3-c]pyridin-5-yl)-1(R)-benzyloxymethyl-2-oxo-ethylcarbamoyl)-1-methyl-ethyl)-carbamic acid tert-butyl ester is prepared.

Another preferred process within Process F is a process wherein a compound of Formula IIA,

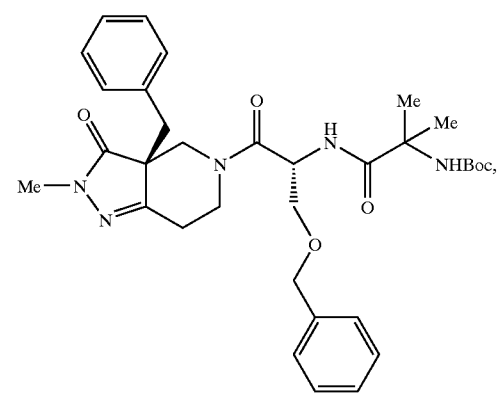

IIA is prepared.

Another preferred process within Process F is a process wherein a compound of Formula IIB,

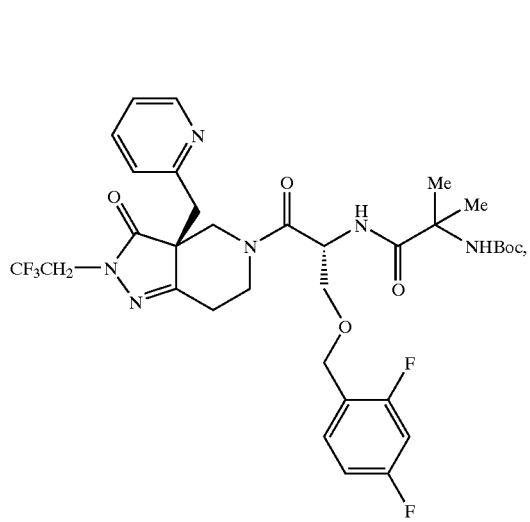

is prepared.

Another preferred process within Process C, designated Process H, is a process wherein: in step a, said organic amine is triethylamine; in step b, $R^3$ is phenylmethyloxymethyl or 2,4-difluorophenylmethyloxymethyl and Prt is t-butyloxycarbonyl; and in step c, said coupling reagent is propane phosphonic acid anhydride.

A preferred process within Process H, designated Process I, wherein $R^1$ is methyl or 2,2,2-trifluoroethyl and $R^2$ is phenylmethyl or 2-pyridylmethyl.

A preferred process within Process I is a process wherein the compound of Formula II selected from (1-(2-(1(R)-(2,4-difluorobenzyloxymethyl)-3a(R)-pyridin-2-ylmethyl-2-(2,2,2-trifluoro-ethyl)-3-oxo-2,3,3a,4,6,7-hexahydro-pyrazolo[4,3-c]pyridin-5-yl)-2-oxo-ethylcarbamoyl)-1-methyl-ethyl)-carbamic acid tert-butyl ester and (1-(2-(3a(R)-benzyl-2-methyl-3-oxo-2,3,3a,4,6,7-hexahydro-pyrazolo[4,3-c]pyridin-5-yl)-1(R)-benzyloxymethyl-2-oxo-ethylcarbamoyl)-1-methyl-ethyl)-carbamic acid tert-butyl ester is prepared.

Another preferred process within Process I is a process wherein a compound of Formula IIA,

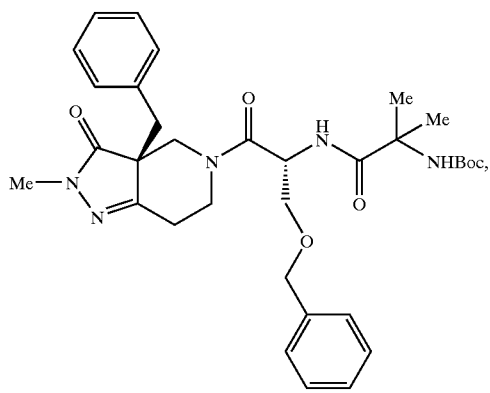

is prepared.

Another preferred process within Process I is a process wherein a compound of Formula IIB,

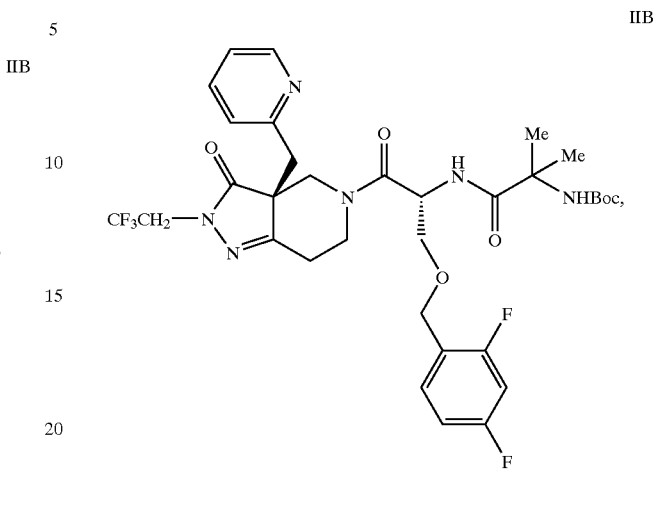

is prepared.

This invention is also directed to a process, designated Process J, for preparing a compound of Formula III,

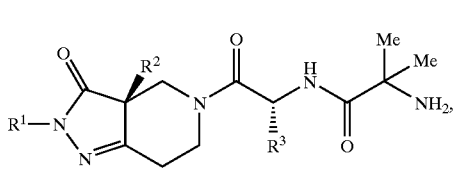

wherein:

$R^1$ is —$(C_1$–$C_{10})$alkyl optionally substituted with up to three fluoro atoms;

$R^2$ is phenylmethyl or 2-pyridylmethyl; and $R^3$ is —$(C_1$–$C_5)$alkyl-O—$(C_0$–$C_5)$alkylphenyl, where the phenyl substituent in the definition of $R^3$ is optionally substituted with up to three fluoro atoms, comprising:

a) mixing an appropriate chiral tartrate salt of the Formula IV,

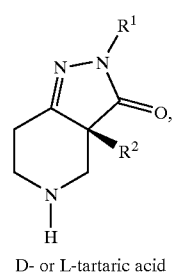

D- or L-tartaric acid wherein $R^1$ and $R^2$ are as defined above, and an organic amine in a reaction inert solvent at a temperature of about −68° C. to about −45° C. to form a slurry;

b) adding a compound of the Formula V,

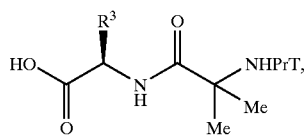

V wherein $R^3$ and Prt are as defined above, to said slurry to form a reaction mixture comprising the tartrate salt of the organic amine, the free base of a compound of Formula IV and a compound of the Formula V;

c) adding a coupling reagent to said reaction mixture to form a compound of Formula II; and d) reacting said compound of Formula II with a suitable deprotecting reagent to form a compound of Formula III.

A preferred process within Process J, designated Process K, is a process wherein said compound of Formula IV is suspended in said solvent prior to the addition of said organic amine and the additional step of warming said slurry to about −50° C. to about −40° C. is effected prior to step b.

A preferred process within Process K, designated Process L, is a process wherein said Prt is Boc and said Boc is removed by reacting said compound of Formula II with an acid.

A preferred process within Process L, designated Process M, is a process wherein said acid is methanesulfonic acid.

A preferred process within Process M, designated Process N, is a process wherein: $R^3$ is phenylmethyloxymethyl or 2,4-difluorophenylmethyloxymethyl; in step b, said organic amine is triethylamine; and in step c), said coupling reagent is propane phosphonic acid anhydride.

A preferred process within Process N, designated Process O, is a process wherein $R^1$ is methyl or 2,2,2-trifluoroethyl and $R^2$ is phenylmethyl or 2-pyridylmethyl.

A preferred process within Process O is a process wherein said compound of Formula III selected from 2-amino-N-[2-(3a(R)-benzyl-2-methyl-3-oxo-2,3,3a,4,6,7-hexahydro-pyrazolo-[4,3-c]pyridin-5-yl-1(R)-benzyloxylmethyl-2-oxo-ethyl]-isobutyramide and 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl-2-methyl-propionamide is prepared.

Another preferred process within Process O is a process wherein a compound of formula IIIA,

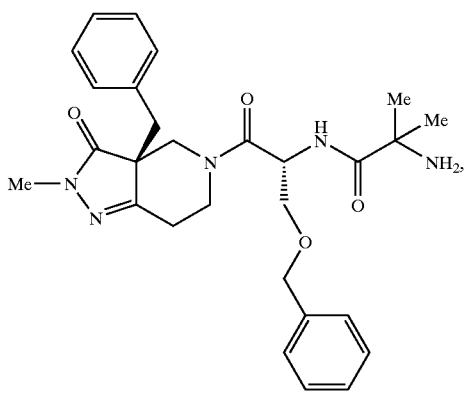

IIIA is prepared.

Another preferred process within Process O is a process wherein a compound of formula IIIB,

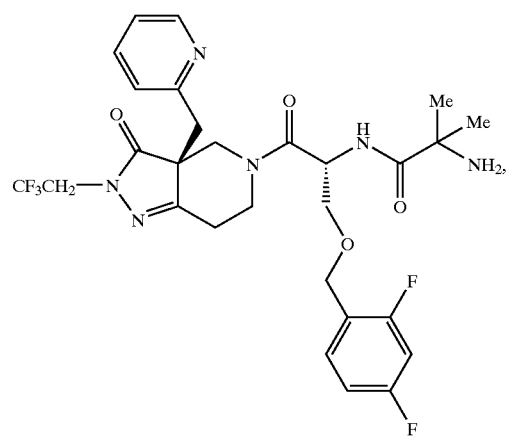

IIIB is prepared.

Another preferred process within Process L, designated Process P, is a process wherein said acid is trifluoroacetic acid.

A preferred process within Process P, designated Process R, is a process wherein: $R^3$ is phenylmethyloxymethyl or 2,4-difluorophenylmethyloxymethyl; in step b, said organic amine is triethylamine; and in step c, said coupling reagent is propane phosphonic acid anhydride.

A preferred process within Process R, designated Process S, is a process wherein $R^1$ is methyl or 2,2,2-trifluoroethyl and $R^2$ is phenylmethyl or 2-pyridylmethyl.

A preferred process within Process S is a process wherein said compound of Formula III selected from 2-amino-N-[2-(3a(R)-benzyl-2-methyl-3-oxo-2,3,3a,4,6,7-hexahydro-pyrazolo-[4,3-c]pyridin-5-yl-1(R)-benzyloxylmethyl-2- oxo-ethyl]-isobutyramide and 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl-2-methyl-propionamide is prepared.

Another preferred process within Process S is a process wherein a compound of formula IIIA,

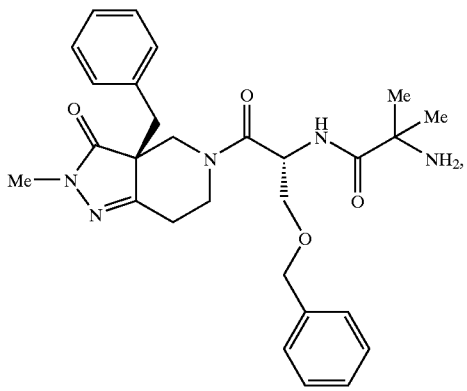

IIIA is prepared.

Another preferred process within Process S is a process wherein a compound of formula IIIB,

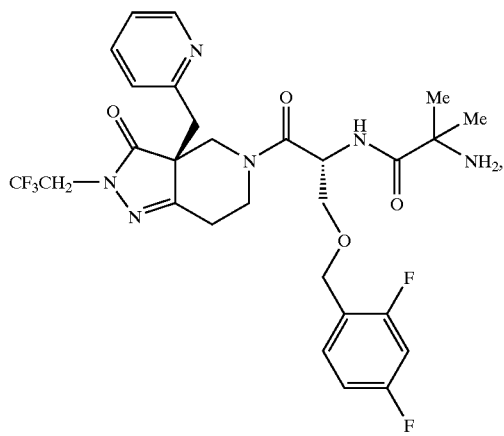

IIIB is prepared.

Another preferred process within claim K, designated Process T, is a process wherein said Prt is Boc and said Boc is removed by reacting said compound of Formula II with an acid.

A preferred process within Process T, designated Process U, is a process wherein said acid is methanesulfonic acid.

A preferred process within Process U, designated Process V, is a process wherein: $R^3$ is phenylmethyloxymethyl or 2,4-difluorophenylmethyloxymethyl; in step b, said organic amine is triethylamine; and in step c, said coupling reagent is propane phosphonic acid anhydride.

A preferred process within Process V, designated Process W, is a process wherein $R^1$ is methyl or 2,2,2-trifluoroethyl and $R^2$ is phenylmethyl or 2-pyridylmethyl.

A preferred process within Process W is a process wherein said compound of Formula III selected from 2-amino-N-[2-(3a(R)-benzyl-2-methyl-3-oxo-2,3,3a,4,6,7-hexahydro-pyrazolo-[4,3-c]pyridin-5-yl-1(R)-benzyloxylmethyl-2-oxo-ethyl]-isobutyramide and 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl-2-methyl-propionamide is prepared.

Another preferred process within Process W is a process wherein a compound of formula IIIA,

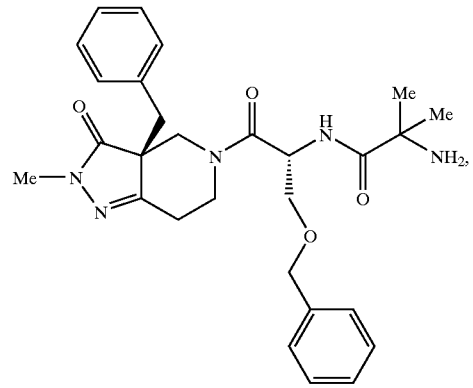

IIIA is prepared.

Another preferred process within Process W is a process wherein a compound of formula IIIB,

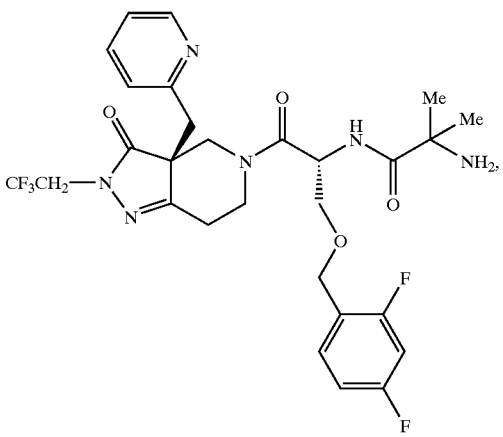

IIIB is prepared.

Another preferred process within Process T, designated Process X, is a process wherein said acid is trifluoroacetic acid.

A preferred process within Process X, designated Process Y, is a process wherein: $R^3$ is phenylmethyloxymethyl or 2,4-difluorophenylmethyloxymethyl; in step b), said organic amine is triethylamine; and in step c, said coupling reagent is propane phosphonic acid anhydride.

A preferred process within Process Y, designated Process Z, is a process wherein $R^1$ is methyl or 2,2,2-trifluoroethyl and $R^2$ is phenylmethyl or 2-pyridylmethyl.

A preferred process within Process Z is a process wherein said compound of Formula III selected from 2-amino-N-[2-(3a(R)-benzyl-2-methyl-3-oxo-2,3,3a,4,6,7-hexahydro-pyrazolo-[4,3-c]pyridin-5-yl-1(R)-benzyloxylmethyl-2-oxo-ethyl]-isobutyramide and 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl-2-methyl-propionamide is prepared.

Another preferred process within Process Z is a process wherein a compound of formula IIIA,

IIIA

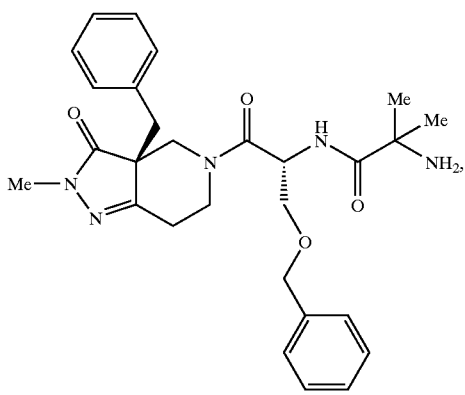

is prepared.

Another preferred process within Process Z is a process wherein a compound of formula IIIB,

IIIB

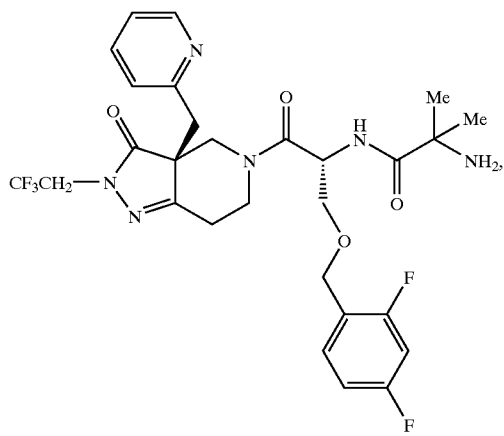

is prepared.

This invention is also directed to a process for preparing a compound of formula XX,

XX

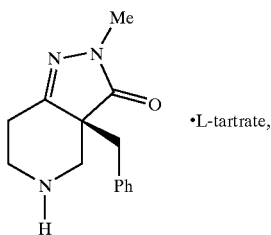

comprising the following consecutive steps:
a) reacting said 4-oxo-piperidinecarboxylic acid methyl ester, hydrochloride with di-t-butyl-dicarbonate and triethylamine in isopropyl ether to form 4-oxo-1,3-piperidinedicarboxylic acid 1-(1-dimethylethyl) 3-methyl ester;
b) reacting said 4-oxo-1,3-piperidinedicarboxylic acid 1-(1-dimethylethyl) 3-methyl ester with benzyl bromide and potassium carbonate in tetrahydrofuran to form 4-oxo-(phenylmethyl)-1,3-piperidinedicarboxylic acid 1-(1-dimethylethyl) 3-methyl ester;
c) reacting said 4-oxo-(phenylmethyl)-1,3-piperidinedicarboxylic acid 1-(1-dimethylethyl) 3-methyl ester with methylhydrazine in acetic acid and methyl-t-butyl ether to form 2,3a,4,5,6,7-hexahydro-2-methyl-3-oxo-3a-(phenylmethyl)-5H-pyrazolo[4,3-c]pyridine-5-carboxylic acid 1,1-dimethylethyl ester; and
d) reacting said 2,3a,4,5,6,7-hexahydro-2-methyl-3-oxo-3a-(phenylmethyl)-5H-pyrazolo[4,3-c]pyridine-5-carboxylic acid 1,1-dimethylethyl ester with trifluoroacetic acid to form (3aR)-2,3a,4,5,6,7-hexahydro-2-methyl-3a-(phenylmethyl)-3H-pyrazolo[4,3-c]pyridin-3-one;
e) reacting said (3aR)-2,3a,4,5,6,7-hexahydro-2-methyl-3a-(phenylmethyl)-3H-pyrazolo[4,3-c]pyridin-3-one with L-tartaric acid in acetone and water to form said L-tartrate salt of formula XX.

This invention is particularly directed to a process as set forth in the immediately preceding paragraph wherein said L-tartaric acid is added without isolating said (3aR)-2,3a,4,5,6,7-hexahydro-2-methyl-3a-(phenylmethyl)-3H-pyrazolo[4,3-c]pyridin-3-one. In particular, the compound of formula XX is isolated as a dihydrate. The desired crystal form is isolated upon cooling from an appropriate mixture of solvents.

This invention is also directed to a polymorph of a dihydrate of a compound of formula XX:

XX

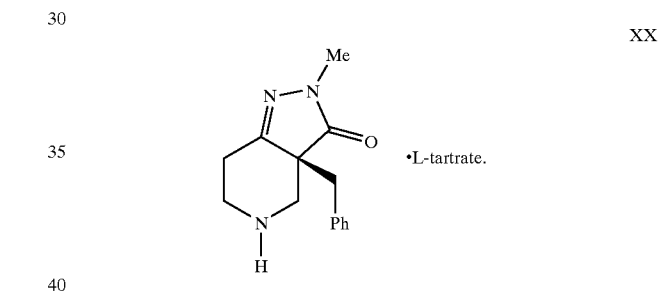

This invention is particularly directed to the polymorph having the atomic coordinates and equivalent isotropic displacement coefficients as set forth in Table 1. This invention is also particularly directed to the polymorph having the X-Ray crystal structure according to FIG. 1.

DETAILED DESCRIPTION OF THE INVENTION

Figure 1:
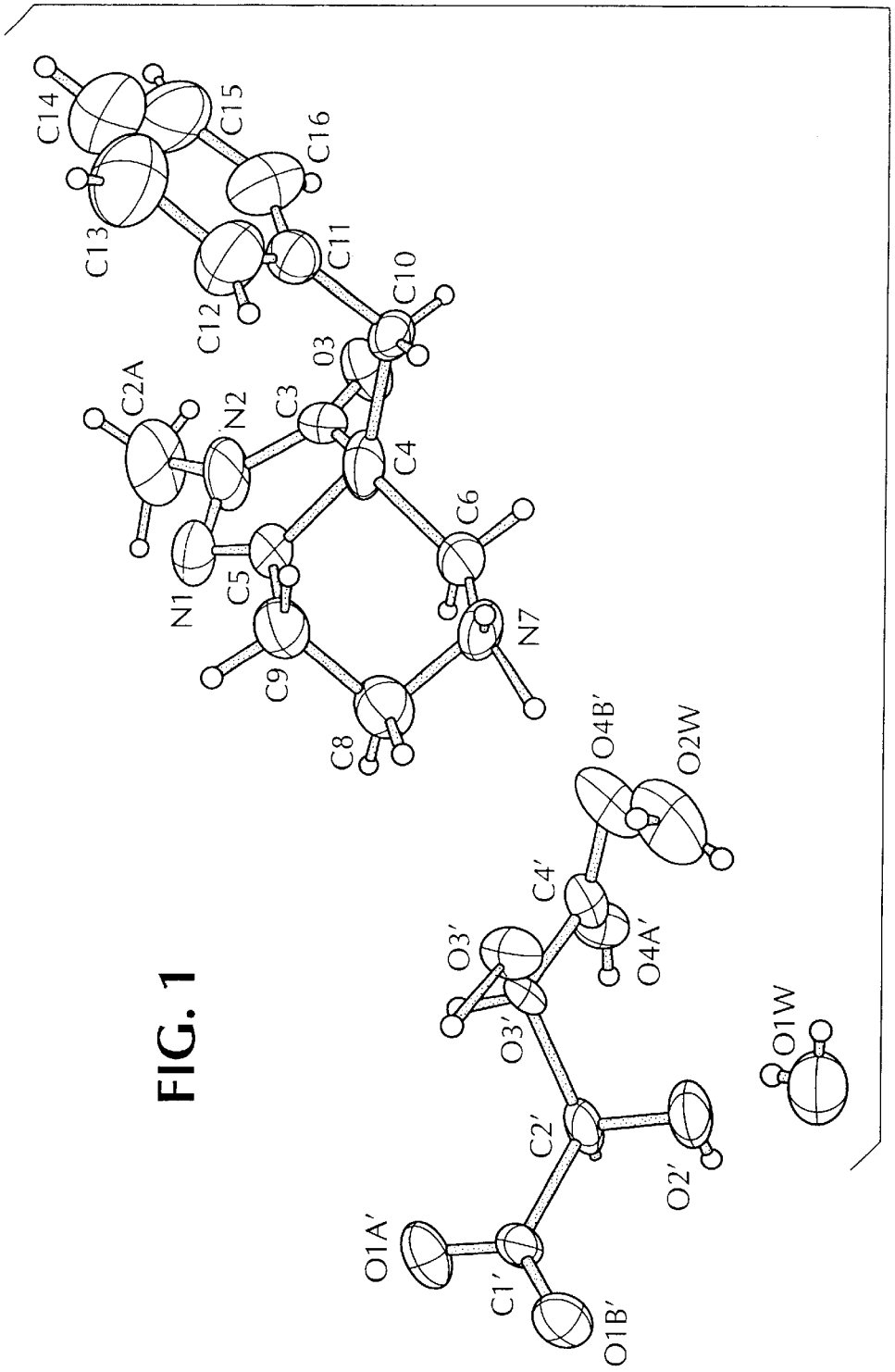
FIG. 1 is an X-Ray crystal structure of the compound of formula XX, collected on a Siemens R3RA/v diffractometer. The crystal structure shows that the compound is a dihydrate of the L-tartrate salt of said compound.

The following schemes illustrate the synthesis of the compounds of Formulas II and III. The symbol "*" indicates a stereochemical center. In the scheme "Prt" is used to indicate any suitable amine protecting group known to those skilled in the art. In the description following each scheme, the amine protecting group Prt is illustrated with the preferred amine protecting group BOC, though it will be recognized that other amine protecting groups may also be utilized.

Scheme 1

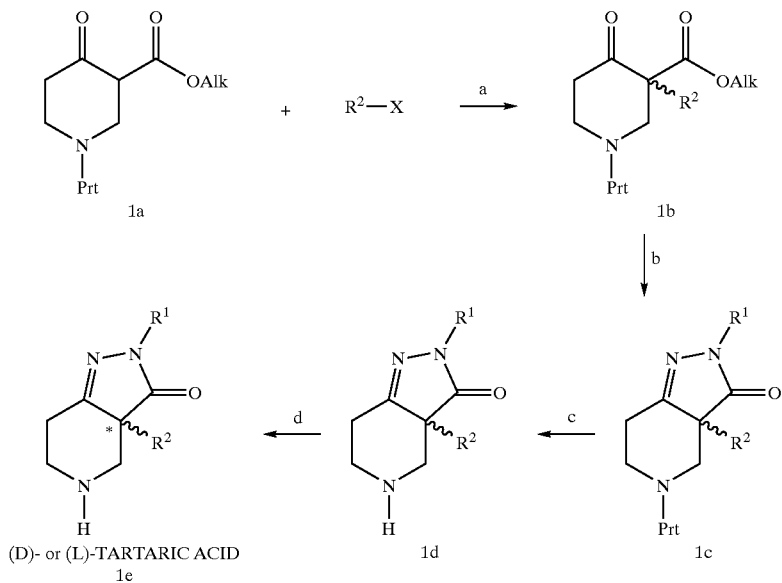

Compounds of Formula IV wherein Alk is methyl or ethyl, $R^1$, $R^2$ and Prt are as defined above, e.g., the compounds of formula 1e, are prepared as set forth in Scheme 1 or 1a. According to Scheme 1, step a, a compound of formula 1a is mixed with a reaction inert polar aprotic solvent such as acetone, methyl ethyl ketone, DMF (dimethylformamide) or preferably tetrahydrofuran at about 0° C. to room temperature, preferably room temperature. To the solution is added $R^2$—X, wherein X is a leaving group such as halo or an alkyl- or aryl-sulfonate; a base such as potassium t-butoxide or a carbonate such as $Li_2CO_3$, $Cs_2CO_3$ or preferably potassium carbonate; and optionally a phase transfer reagent such as potassium iodide or tetrabutylammonium iodide. In the case where postassium carbonate is used as base, it is preferred that a phase transfer reagent is not used. It is preferred that, where $R^2$ is benzyl, $R^2$—X is benzyl bromide and that where $R^2$ is 2-pyridylmethyl, $R^2$—X is picolyl chloride hydrochloride. After stirring at about −20° C. to about 70° C. for about 2 to 16 hours, preferably at 60° C. to about 65° C. for about 12 hours, the product is isolated from the reaction mixture according to techniques well known to those skilled in the art. This step is preferably carried out as set forth in Preparation Five, Step D, below.

According to step b, a hydrazine derivative is reacted with a compound of formula 1b. Preferably the hydrazine derivative is a 70% aqueous solution of $CF_3CH_2NHNH_2$ (trifluoroethylhydrazine) or anhydrous $CH_3NHNH_2$ (methylhydrazine) which is used as an aqueous solution in ethanol, water or toluene. When the 70% solution of trifluoroethylhydrazine is used, it is further preferred that the 70% aqueous solution of $CF_3CH_2NHNH_2$ is extracted with toluene. To a solution of a compound of formula 1b in an organic solvent such as ethanol, toluene or preferably methyl t-butylether (MTBE), is first added the anhydrous 2,2,2-trifluoroethyl hydrazine or methyl hydrazine, followed by acetic acid. Preferably, MTBE is used to prevent the reaction mixture from reaching a dangerously high temperature. The reaction mixture is heated at about 50° C. to about 110° C. for about 30 minutes to 24 hours, preferably about 60° C. for about 12 to about 15 hours. The reaction mixture is cooled to room temperature and neutralized with an aqueous base such as $NaHCO_3$. Where used herein, the term "room temperature" means a temperature of about 20° C.–25° C. The organic layer is separated and worked up using standard methods known in the art to yield a compound formula 1c. This step is preferably carried out as set forth in Preparation Five, Step E, below.

According to step c, an acid such as HCl in IPE or ethanol, trifluoroacetic acid (TFA) or an alkyl sulfonic acid such as methanesulfonic acid is added to a solution of a compound of formula 1c in a reaction inert organic solvent such as EtOH, IPE or preferably $CH_2Cl_2$. The mixture is stirred for about 1 to 12 hours, then cooled to about 0° C. to about room temperature, preferably to room temperature. After the reaction is complete, a base such as triethylamine or $NH_4OH$ is added to the mixture. The mixture is allowed to warm to room temperature, is diluted with additional organic solvent and worked up using standard methods known in the art to yield a compound of formula 1d. Alternatively and preferably, the compound of formula 1d may be used without isolation in the next step. Step c of Scheme 1 is preferably carried out in combination with step d of Scheme 1 as set forth in Preparation Five, Step F, below.

According to step d, (D)- or (L)-tartaric acid, preferably (L)-tartaric acid, is added to a compound of formula 1d in acetone/water (about 8:1 to about 9:1) at about room temperature. The mixture is stirred at about room temperature to about the reflux temperature of the solvent mixture for about 1 hour to overnight, e.g., 18 hours, preferably 15 to 18 hours. Preferably the compound of formula 1e is isolated as a dihydrate crystal form. Then the solid is filtered, collected and washed with cold acetone, to yield a compound of formula 1e, which is preferably the (L)-tartrate of a single enantiomer. This step is preferably carried out as set forth in Preparation Five, Step F, without isolation of the precursor free base compound.

Scheme 1a
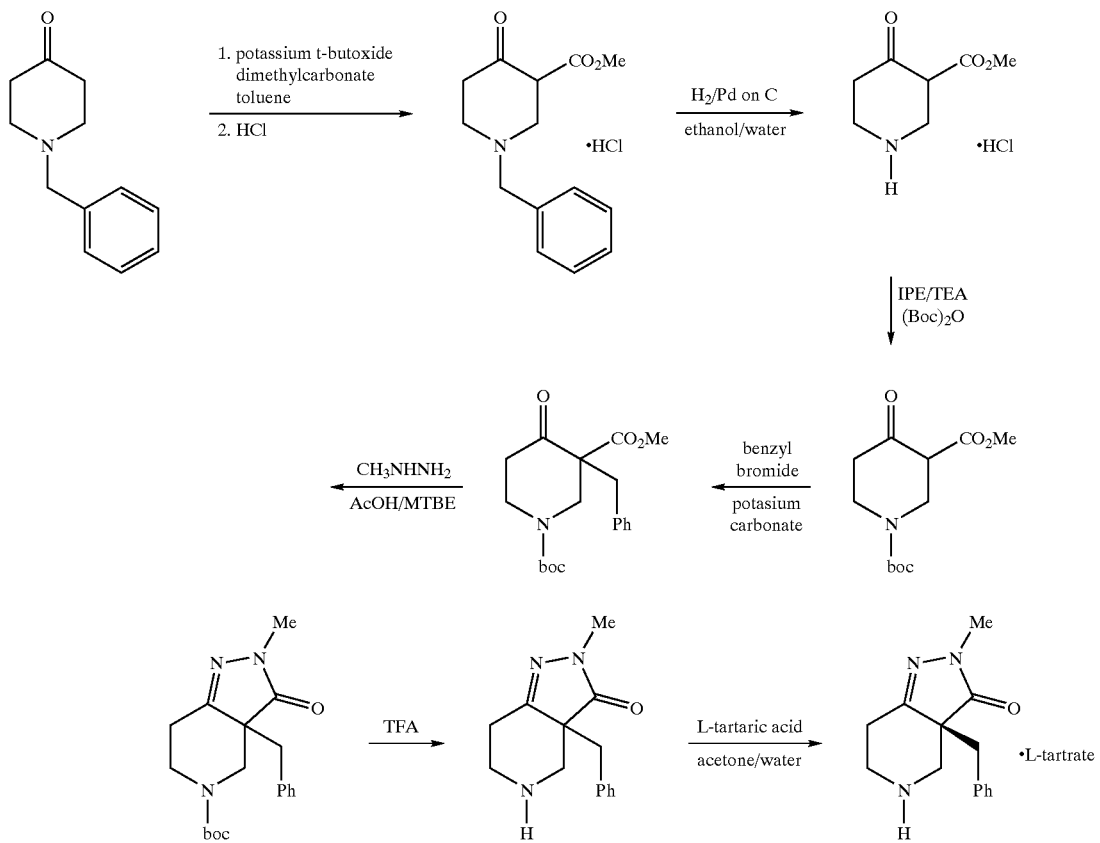
Scheme 2
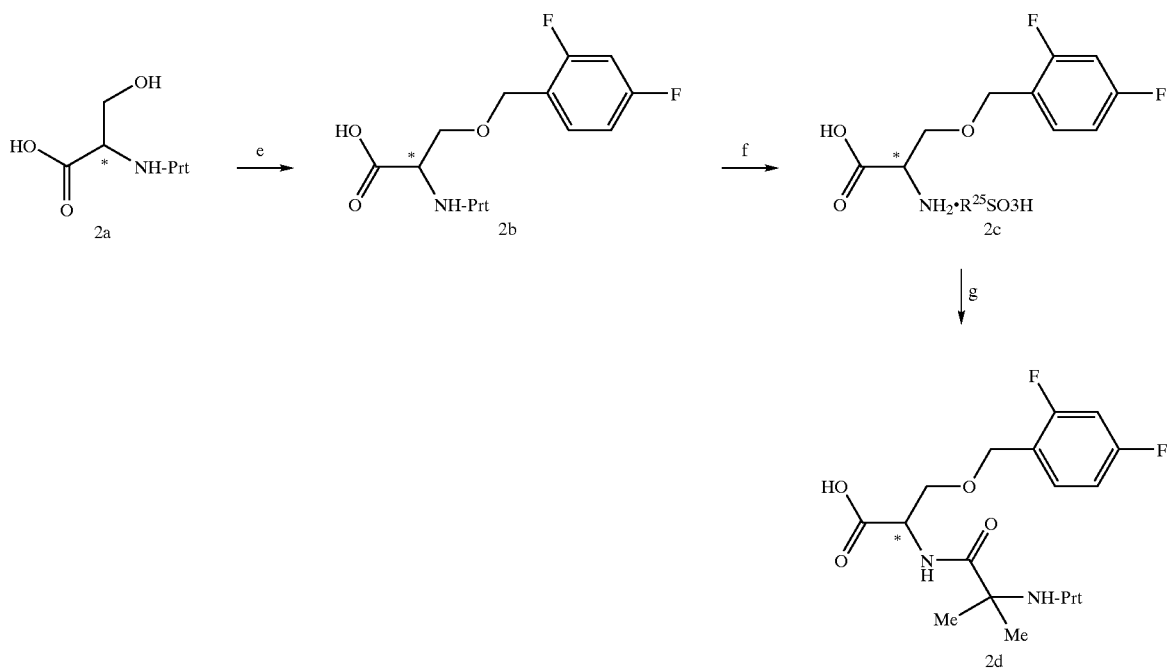

Compounds of formula V wherein $R^3$ is difluorobenzyloxymethyl, $R^{25}$ is alkyl, aryl or substituted aryl and Prt is an amine protecting group, e.g., the compounds of formula 2d, are prepared as set forth in Scheme 2. According to step e, to a solution of N-BOC-serine, preferably N-BOC-(D)-serine, the compound of formula 2a, in THF/DMF (about 1:1 to about 2:1) at about 0° C. is added n-BuLi or a potassium tert-butoxide solution. The reaction mixture is stirred at about 0° C. for about 10 to about 30 minutes, preferably for 20 minutes, then 2,4-difluorobenzyl bromide is added. After warming to room temperature and stirring for about 6 to about 24 hours, the reaction mixture is concentrated in vacuo to remove the THF and an aqueous acid such as 1 N HCl is added to adjust the mixture to pH of about 3. The reaction mixture is then partitioned between water and an organic solvent such as methylene chloride ($CH_2Cl_2$) or IPE. The organic solution is worked up using standard methods known in the art to yield the compound of formula 2b, preferably having the R-configuration at the stereocenter, also known as the (D)-enantiomer.

According to step f, to a solution of the compound of formula 2b in an organic solvent such as THF, $CH_2Cl_2$, IPE or a mixture thereof, preferably $CH_2Cl_2$/IPE (about 1:1), is added an alkyl or aryl sulfonic acid such as methanesulfonic acid. The solid is filtered and washed with a $CH_2Cl_2$/IPE mixture (1:1) to afford the compound of formula 2c, preferably having the R-configuration at the stereocenter, also known as the (D)-enantiomer.

According to step g, to a solution of the compound of formula 2c in THF/water (about 4:1) is added 2-tert-butoxycarbonylamino-2-methyl-propionic acid-2,5-dioxo-pyrrolidin-1-yl ester and an alkyl amine such as triethylamine. The reaction mixture is stirred at room temperature for about 1–24 hours and quenched with an aqueous acid such as 10% aqueous citric acid solution. The mixture is partitioned with an organic solvent such as ethyl acetate and the organic layer is separated and worked-up using standard methods known in the art to yield a compound of formula 2d, preferably having the R-configuration at the stereocenter also known as the (D)-enantiomer.

The compound of Formula V wherein $R^3$ is benzyloxymethyl and Prt is Boc is prepared as set forth in Preparation Three, Steps A and B, below. Compounds wherein Prt is an amine protecting group other than Boc are prepared by substituting the appropriate N-protected α-methylalanine derivative for N-t-butyloxycarbonyl-α-methylalanine. Appropriate N-protected α-methylalanine derivatives, if not readily available from vendors, can be readily prepared from α-methylalanine according to methods well known to those skilled in the art.

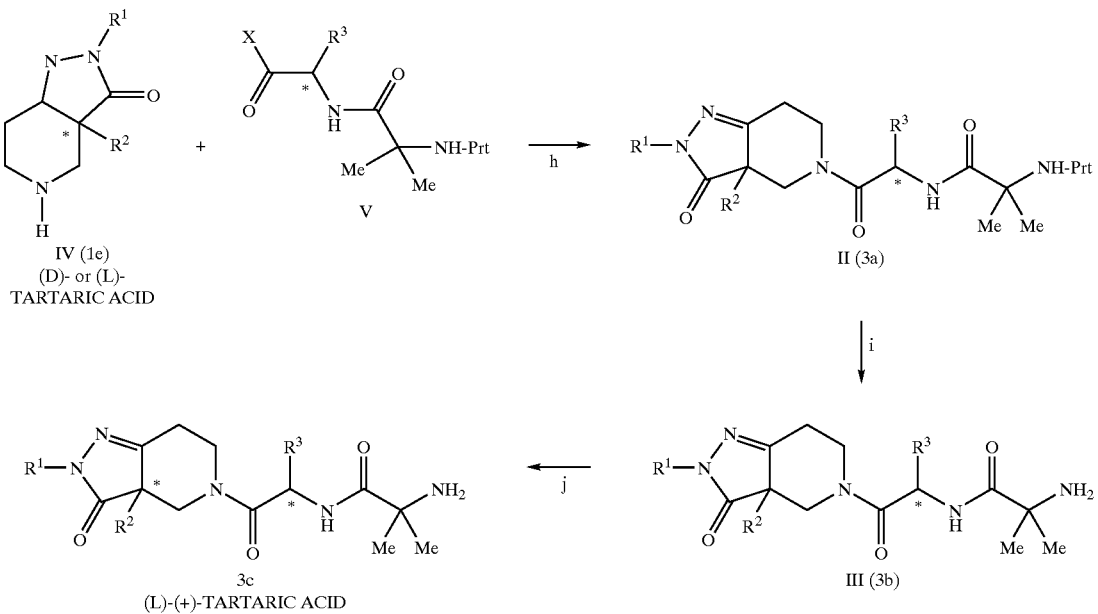

Compounds of formulas II, III and 3c wherein $R^1$, $R^2$ and $R^3$ are as defined above are prepared according to Scheme 3. According to step h, a compound of formula IV (1e), preferably the (L)-tartrate salt of a single enantiomer, is slurried at about −68° C. to about −45° C., preferably at about −68° C. to about −60° C. and most preferably at about −68° C. with a reaction inert solvent, preferably ethyl acetate. An organic amine, such as diisopropylethylamine, trimethylamine or triethylamine, preferably triethylamine, is added. During the addition of the organic amine, the temperature is maintained at about −68° C. to about −45° C. and preferably at about −68° C. to about −60° C. The reaction mixture is stirred for about 30 to about 120 minutes at a temperature between about −78° C. and about −45° C. The resulting slurry contains a mixture of the free base of a compound of Formula IV and an organic amine salt of tartaric acid. To this slurry is added an organic amine such as diisopropylethylamine, trimethylamine or triethylamine, preferably triethylamine. During this addition, the internal temperature of the reaction mixture is maintained below −50° C. To this reaction mixture, which still contains an organic amine salt of tartaric acid, is added a compound of Formula V, all at once, while maintaining the temperature of the reaction mixture at about −68° C. to about −45° C. Then a coupling reagent such as propane phosphonic acid anhydride is added over a period of about 5 minutes to about 30 minutes. The temperature is allowed to warm gradually to about −25° C. to about 0° C., preferably to about −20° C. over the next hour. The reaction mixture is worked up using standard methods known in the art to yield a compound of Formula II, preferably having the absolute and relative 3a(R), 1(R) configuration.

According to step i, an acid such as HCl in EtOH, or methanesulfonic acid or trifluoroacetic acid in $CH_2Cl_2$ is added at about 0° C. to room temperature to a compound of Formula II in a reaction inert solvent such as $CH_2Cl_2$, IPE or THF. The mixture is stirred for about 40 minutes to about 4 hours at room temperature, then a saturated aqueous base such as $Na_2CO_3$ or $NaHCO_3$ is added until the solution is at neutral (7.0) pH. The organic layer is separated and worked up using standard methods known in the art to yield a compound of Formula II, preferably having the absolute and relative 3a(R), 1(R) configuration.

According to step j, to a solution of a compound of Formula III in an alcohol such as methanol, ethanol or isopropanol, preferably isopropanol, is added L-(+) tartaric acid. When methanol or ethanol is used, the reaction mixture is stirred for about 1 hour to about 12 hours and is then filtered and the filtrate is concentrated. In either case, the crude residue is diluted with an organic solvent such as ethyl acetate, heated and slowly allowed to cool to room temperature. The solid is filtered and dried to give the L-(+) tartaric acid salt of the compound of formula 3c, preferably having the absolute and relative 3a(R), 1(R) configuration.

The starting materials and reagents used in the processes of this invention can be purchased from common vendors or prepared according to methods well known to those skilled in the art of organic chemistry. In particular, 4-oxo-(phenylmethyl)-3-piperidinecarboxylic acid methyl ester, hydrochloride may be prepared as set forth in Preparation Five, Step A below or, alternatively, may be prepared as set forth in Hoffman, N. and Erinjeri, A., J. Heterocyclic Chem., 1965, 2, 326.

Where used herein, the term "reaction inert solvent" means a solvent which does not interact with starting materials, reagents, intermediates or products in a manner which adversely affects the yield of the desired product. Said reaction inert solvent in step a is a solvent in which the free base of the compound of Formula IV is soluble.

Where used herein, the term "organic amine" means a lower alkyl amine, such as triethylamine, trimethylamine or diisopropylethylamine; or a cyclic amine, such as piperidine, pyrrolidine or N-methylmorpholine.

The following examples are provided for the purpose of further illustration only and are not intended to be a limitation on the disclosed invention.

Silica gel was used for column chromatography. Melting points were taken on a Buchi 510 apparatus and are uncorrected. Proton NMR spectra were recorded on a Varian XL-300, Bruker AC-300, Varian Unity 400 or Bruker AC-250 at 25° C. Those skilled in the art of organic chemistry will recognize that the NMR data obtained herein can also be obtained on other NMR insturments which are obtainable from a variety of vendors well known to those skilled in the art. Chemical shifts are expressed in parts per million down field from trimethylsilane.

General Procedure A: (Cleavage of a Boc-protecting group from a Boc-protected amine using concentrated HCl): The Boc-protected amine is dissolved in a minimum volume of ethanol and the resulting solution is cooled to about 0° C. and concentrated HCl (typically about 1 to 4 mL per mmol of Boc-protected amine) is added and the reaction mixture is warmed to room temperature and stirred for about one hour to about 2.5 hours (or the time required for complete disappearance of the starting material to a more polar product as judged by thin layer chromatography). The resulting solution or suspension is concentrated and the residue is coevaporated several times with added ethanol to afford the free amine which is used without further purification or purified as specified.

EXAMPLE 1

(1-(2-(3a(R)-Benzyl-2-methyl-3-oxo-2.3,3a.4,6.7-hexahydro-pyrazolo[4,3-c]pyridin-5-yl)-1(R)-benzyloxymethyl-2-oxo-ethylcarbamoyl)-1-methyl-ethyl)-carbamic Acid tert-Butyl Ester

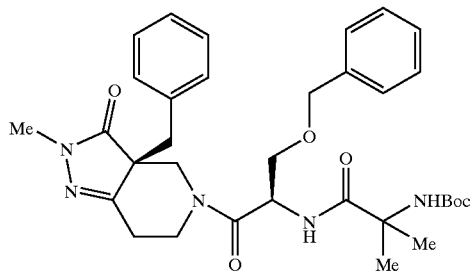

To a dry, nitrogen purged 1 liter, 4 neck, round bottom flask, equipped with a mechanical stirrer, a nitrogen capped condenser, a thermocouple, and an addition funnel was added 3a-benzyl-2-methyl-2,3,3a,4,6,7-hexahydro-pyrazolo [4,3-c]pyridin-3-one (L)-tartrate (prepared according to Preparation One, Step D, 66.09 g, 0.168 moles, 1.12 equivalents) and ethyl acetate (660 mL, 10 volumes). A slurry formed. The slurry was agitated and cooled to an internal temperature of −68° C. to −66° C. To the cooled, agitated slurry was added triethyl amine (TEA, 58 mL, 42.5 g, 0.42 moles, 2.8 equivalents) via the addition funnel. The internal temperature was maintained at −68° C. to −66° C. during addition. The reaction mixture was agitated for about 1.5 hours while the internal temperature was warmed to about −52° C. To the reaction mixture (which was a slurry of the tartrate salt of triethylamine and the free base of 3a-benzyl-2-methyl-2,3,3a,4,6,7-hexahydro-pyrazolo[4,3-c]pyridin-3-one (L)-tartrate) was added triethylamine (96.5 ml, 70 g, 0.69 moles, 4.6 equivalents) over 5 minutes. An internal temperature of −53° C. to −50° C. was maintained during addition. To the reaction mixture was added 3-benzyloxy-2-(2-tert-butoxycarbonylamino-2-methyl-propionylamino)-propionic acid (prepared according to Preparation Three, Step B, 57.07 g, 0.150 moles, 1.0 equivalents), all in one portion. An internal temperature −55° C. to −50° C. was maintained during addition. To the reaction mixture was added propane phosphonic acid anhydride (PPAA, 180 ml, 190 g, 2.0 equivalents) as a 50% solution of propane phosphonic acid anhydride in ethyl acetate. The PPAA was added over 15 minutes and the internal temperature rose to about −30° C. during the addition. The reaction mixture was agitated at about −30° C. for about 0.5 hours. The reaction mixture was poured into a vigorously agitated mixture of diisopropyl ether (IPE, 660 mL, 10 volumes) and water (660 mL, 10 volumes). The resulting biphasic mixture was agitated for 1 hour and then the reaction mixture was allowed to settle. The aqueous portion was decanted and the organic portion was then washed sequentially with aqueous HCl (1N, 165 mL, 2.5 volumes, 1.3 equivalents), 10% aqueous $Na_2CO_3$ (330 mL, 5 volumes, 2.1 equivalents), and 15% aqueous NaCl (165 mL). The washed organic portion was concentrated in vacuo to the lowest stirrable volume and to the concentrate was added IPE (300 mL, about 5 volumes). The solution was again concentrated in vacuo to the lowest stirrable volume. To the concentrate was added IPE (330 mL, about 5 volumes) and the solution was heated atmospherically to an internal temperature of about 67° C. Precipitates were observed and the slurry was cooled to an internal temperature of about 1° C. over 1 hour with agitation. The solids were filtered and dried in vacuo at about 50° C. to afford 54.85 g of the title compound (60.4% yield).

EXAMPLE TWO

2-Amino-N-[2-(3a(R)-benzyl-2-methyl-3-oxo-2,3,3a,4,6,7-hexahydro-pyrazolo-[4,3-c]pyridin-5-yl-1(R)-benzyloxylmethyl-2-oxo-ethyl]-isobutyramide (L-Tartrate Salt)

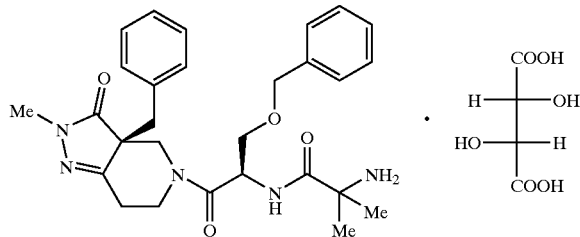

To a 5L, 4 neck, round bottom flask equipped with a mechanical agitator, thermocouple, a condenser and an addition funnel, was added consecutively 3a(R)-benzyl-2-methyl-2,3,3a,4,6,7-hexahydro-pyrazolo[4,3-c]pyridin-3-one (L)-tartrate (prepared according to Preparation One, Step D, 60.57 g, 0.10 moles, 1.0 equivalent) and methylene chloride (400 ml, 6.7 volumes). The mixture was agitated to afford a clear solution and the solution was then cooled to an internal temperature of −10° C. to −5° C. To the cooled, agitated solution was added trifluoroacetic acid (TFA, 180 ml, 3.0 volumes/23.6 equivalents/2.33 moles) at such a rate that the internal temperature did not exceed −5° C. The addition was complete in about 10 minutes. The reaction mixture was then slowly warmed to 8° C. over 1 hour. While maintaining an internal temperature of 10° C.–20° C., the reaction mixture was brought to pH greater than 8 by slow addition of $Na_2CO_3$ (1.0 N, 1200 ml, 12 equivalents/12 moles). The reaction mixture was allowed to settle and the organic portion was decanted. The aqueous fraction was extracted with methylene chloride (2×100 ml portions, 1.65 volumes each). The combined organic fractions were washed with water (100 mL). The washed organic fraction was concentrated to the lowest stirrable volume by atmospheric distillation and to the concentrate was added ethyl acetate (2000 ml, 33 volumes). To the ethyl acetate solution was added a solution L-tartaric acid (15.05 g, 0.10 moles/1 equivalent) in methanol (60 ml, 1 volume). The reaction mixture was heated and the methanol distilled off. The distillation was continued until the internal and head temperature were 77° C.–78° C. and then the reaction mixture was refluxed for 1–2 hours. The reaction was then cooled to about 1 5° C. over several hours. The solids were filtered, washed with ethyl acetate (200 ml) and dried overnight in vacuo at about 50° C. to afford 60.79 g of the title compound (92.7% yield).

EXAMPLE THREE (1-(2-(1(R)-(2,4-Difluorobenzyloxymethyl)-3a(R)-pyridin-2-ylmethyl-2-(2,2,2-trifluoroethyl)-3-oxo-2,3,3a,4,6,7-hexahydro-pyrazolo[4,3-c]pyridin-5-yl)-2-oxo-ethylcarbamoyl)-1-methyl-ethyl)-carbamic Acid tert-Butyl Ester

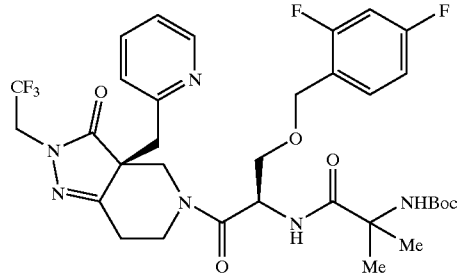

To a dry, nitrogen purged 0.5 liter, 4 neck, round bottom flask, equipped with a mechanical stirrer, a nitrogen capped condenser, a thermocouple, and an addition funnel were added sequentially 3a-pyridin-2-ylmethyl-2-(2,2,2-trifluoroethyl)-2,3a,4,5,6,7-hexahydro-pyrazolo[4,3-c]pyridin-3-one (L)-tartrate (prepared according to Preparation Two, Step D, 10.35 g, 0.0224 moles, 1.12 equivalents) and ethyl acetate (110 mL, 10 volumes). A slurry formed. The slurry was agitated and cooled to an internal temperature of −68° C. to −60° C. To the cooled, agitated slurry was added triethylamine (TEA, 7.75 ml, 5.66 g, 0.056 moles, 2.8 equivalents) via the addition funnel. The internal temperature was maintained at −68° C. to −60° C. during addition. The reaction mixture was agitated for about 1.5 hours while the internal temperature was warmed to about −62° C. to −52° C. To the reaction mixture (which was a slurry of the tartrate salt of triethylamine and the free base of 3a-pyridin-2-ylmethyl-2-(2,2,2-trifluoroethyl)-2,3a,4,5,6,7-hexahydro-pyrazolo[4,3-c]pyridin-3-one (L)-tartrate) was added triethylamine (12.7 ml, 9.30 g, 0.092 moles, 4.6 equivalents) over 5 minutes. An internal temperature of −62° C. to −50° C. was maintained during addition. To the reaction mixture was added 2-(2-tert-butoxycarbonylamino-2-methyl-propionylamino)-3-(2,4-difluoro-benzyloxy)-propionic acid (prepared according to Preparation Four, Step C, 8.34 g, 0.020 moles, 1.0 equivalents), all in one portion. An internal temperature of −60° C. to −58° C. was maintained during addition. Propane phosphonic acid anhydride (PPM, 24 mL, 25.5 g, 2.0 equivalents) as a 50% solution of propane phosphonic acid anhydride in ethyl acetate was diluted with ethyl acetate (24 mL, 2.2 volumes) and cooled to about −45° C. The PPM solution was then added to the reaction mixture. The PPM was added over 15 minutes and the internal temperature rose gradually to about −19° C. over about 1 hour. The reaction mixture was poured into a vigorously agitated mixture of diisopropyl ether (IPE, 100 mL, 9.1 volumes) and water (100 mL, 9.1 volumes). The resulting biphasic mixture was agitated for 5 minutes and then the reaction mixture was allowed to settle. The aqueous portion was decanted and the organic portion was then washed sequentially with aqueous HCl (0.5N, 50 mL, 4.5 volumes, 1.3 equivalents), saturated aqueous $NaHCO_3$ (50 mL, 4.5 volumes, ~2.5 equivalents), and 15% aqueous NaCl (50 mL). The washed organic portion was concentrated in vacuo to afford an oil. The oil was agitated with hexanes (50 mL, about 2.5 volumes) to afford a glassy solid, 13.75 g (96.8% crude yield). The solids were dissolved in chloroform and concentrated in vacuo to afford an oil. This procedure was repeated with hexanes. Finally, the resultant oil was agitated with hexanes for 16 hours. The resultant solids were filtered to afford 10.45 g of the title compound (73.6% yield).

EXAMPLE FOUR

2-Amino-N-(1(R)-(2.4-difluoro-benzyloxmethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl)-2-methyl-propionamide

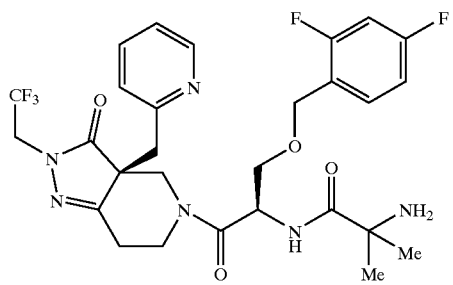

(1-(2-(1(R)-(2,4-Difluorobenzyloxymethyl)-3a(R)-pyridin-2-ylmethyl-2-(2,2,2-trifluoro-ethyl)-3-oxo-2,3,3a,4,6,7-hexahydro-pyrazolo[4,3-c]pyridin-5-yl)-2-oxo-ethylcarbamoyl)-1-methyl-ethyl)-carbamic acid tert-butyl ester (prepared according to Example Three, 17.5 g, 25.3 mmol) was deprotected according to the method described in General Procedure A to afford a colorless solid. The product was triturated with diethyl ether to afford the title compound. (13.6 g, 90%):+Apcl MS (M+H)+591.

EXAMPLE FIVE

Example Five

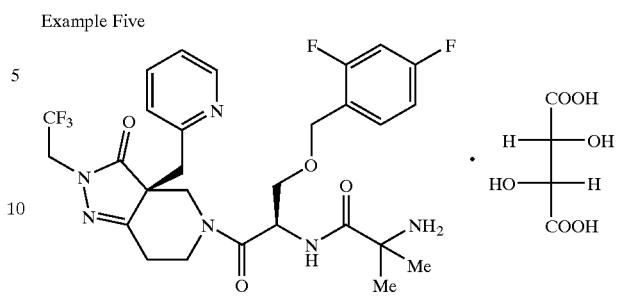

2-Amino-N-{1-(2,4-difluoro-benzyloxymethyl)-2-oxo-2-[3-oxo-3a(R)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide L-(+) Tartrate To a solution of 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl)-2-methyl-propionamide (prepared according to Example Four, 370 g, 0.6 mol) in methanol (4,070 mL) in a 12 L round bottom flask equipped with a mechanical stirrer was added L-(+) tartaric acid (90 g, 0.6 mol). The reaction mixture was stirred for about 90 min. at about 22° C., filtered and concentrated. The crude residue was diluted with ethyl acetate (4,560 mL), heated at about 70° C. and slowly allowed to cool to room temperature over about 17 hours. The solid was filtered and dried to give white crystals, mp 188–189° C. (348.46 g, yield 76%). $^1$H NMR (MeOH, d4) δ: 8.28 (d, 1H), 7.59 (t, 1H), 7.41–7.39 (m, 1H), 7.18–7.13 (m, 1H), 6.92 (t, 1H), 5.2 (t, 1H), 4.56 (bs, 3H), 4.36 (s, 2H), 4.31–4.25 (m, 1H), 4.13–4.06 (m, 1H), 3.78 (d, 2H), 3.21 (t, 1H), 3.18–2.96 (m, 2H), 2.65–2.55 (m, 2H), 1.57 (d, 6H). MS: MH+ 611. $[a]^{589}$+22.03 (c=11.9, MeOH).

EXAMPLE SIX

Single Crystal X-Ray Analysis. A representative crystal was surveyed and a 1 Å data set (maximum θ/λ=0.5) was collected on a Siemens $R^3RA/V$ diffractometer. Atomic scattering factors were taken from the International Tables for X-Ray Crystallography.[1] All crystallographic calculations were facilitated by the SHELXTL[2] system. All diffractometer data were collected at room temperature. Pertinent crystal, data collection, and refinement parameters are summarized in Table I below.

A trial structure was obtained by direct methods. This trial structure refined routinely. Hydrogen positions were calculated wherever possible. The methyl hydrogens and the hydrogens on the nitrogen and oxygen were located by difference Fourier techniques. The hydrogen parameters were added to the structure factor calculations but were not refined. The shifts calculated in the final cycle of least squares refinement were all less than 0.1 of their corresponding standard deviations. The final R-index was 4.95%. A final difference Fourier revealed no missing or misplaced electron density.

The refined structure was plotted using the SHELXTL plotting package (FIG. 1). The absolute configuration was assigned on the known configuration of L-tartaric acid. Coordinates, anisotropic temperature factors, distances and angles are available as supplementary material, see Tables II through VI.

TABLE I

Single Crystal X-Ray Crystallographic Analysis

A. Crystal Parameters:

| | |
|---|---|
| formula | $C_{14}H_{18}N_3O^+$ $C_4H_5O_6^- \cdot 2H_2O$ (429.4) |
| crystallization medium | acetone and water (4:1) |
| crystal size, mm | 0.05 × 0.12 × 0.32 |
| cell dimensions | a = 8.235 (3) Å |
| | b = 7.032 (2) Å |
| | c = 18.106 (6) Å |
| | α = 90.0° |
| | β = 99.41 (2)° |
| | γ = 90.0° |
| | V = 1034.4 (6) Å³ |
| space group | $P2_1$ |
| molecules/unit cell | 2 |
| density calcd, g/cm³ | 1.379 |
| linear absorption factor, mm⁻¹ | 0.946 |

B. Refinement Parameters:

| | |
|---|---|
| number of reflections | 1174.39 |
| nonzero reflections (I > 3.0σ) | 1025 |
| R-index[a] | 4.95% |
| GOF[b] | 1 |
| secondary extinction factor[c], $\chi 52$ (8) × $10^{-4}$ | | a  R-index = Σ ‖ Fo | − | Fc |/Σ | Fo |
b  GOF = [Σw(Fo² − Fc²)²/(m − s)]^½
   where w = [σ² (F) + | g | F²]⁻¹ and g = 0.0005
c  F* = F[1 + 0.002$_\chi$F²/sin(2θ)]^−¼

TABLE II

Atomic coordinates (×10⁴) and equivalent isotropic displacement coefficients (Å² × 10³)

| | x | y | z | U(eq) |
|---|---|---|---|---|
| C(1') | 7050 (7) | 12045 (7) | 6424 (4) | 31(1) |
| O(1A') | 5715 (5) | 12748 (6) | 6097 (3) | 41(1) |
| O(1B') | 8234 (5) | 12946 (6) | 6748 (3) | 41(1) |
| C(2') | 7120 (6) | 9881 (7) | 6388 (4) | 29(1) |
| O(2') | 8733 (5) | 9232 (6) | 6715 (3) | 37(1) |
| C(3') | 6707 (7) | 9167 (7) | 5599 (4) | 32(1) |
| O(3') | 7899 (5) | 9726 (6) | 5160 (3) | 47(1) |
| C(4') | 6647 (6) | 6999 (7) | 5583 (4) | 32(1) |
| O(4A') | 5644 (5) | 6263 (6) | 5971 (3) | 39(1) |
| O(4B') | 7465 (5) | 6110 (7) | 5213 (3) | 59(1) |
| N(1) | 5011 (6) | 8379 | 1995 (3) | 43(1) |
| N(2) | 4317 (6) | 6558 (7) | 1896 (3) | 40(1) |
| C(2A) | 2623 (6) | 6380 (8) | 1541 (4) | 55(1) |
| C(3) | 5357 (7) | 5149 (8) | 2171 (4) | 36(1) |
| O(3) | 5039 (5) | 3491 (6) | 2188 (3) | 46(1) |
| C(4) | 6998 (6) | 6172 (8) | 2450 (3) | 28(1) |
| C(5) | 6515 (6) | 8177 (8) | 2299 (4) | 33(1) |
| C(6) | 7511 (6) | 5878 (8) | 3290 (4) | 39(1) |
| N(7) | 8723 (6) | 7355 (7) | 3591 (3) | 40(1) |
| C(8) | 8153 (7) | 9366 (8) | 3440 (4) | 49(1) |
| C(9) | 7643 (7) | 9700 (8) | 2603 (4) | 46(1) |
| C(10) | 8290 (6) | 5440 (8) | 1989 (4) | 37(1) |
| C(11) | 7862 (7) | 5776 (8) | 11667 (4) | 43(1) |
| C(12) | 8463 (7) | 7317 (8) | 853 (4) | 69(1) |
| C(13) | 8108 (8) | 7675 (9) | 76 (5) | 97(1) |
| C(14) | 7080 (*) | 6405 (9) | −336 (5) | 96(1) |
| C(15) | 6443 (8) | 4882 (8) | −59 (5) | 81(1) |
| C(16) | 6872 (8) | 4533 (8) | 705 (4) | 75(1) |
| O(1W) | 8100 (5) | 6278 (7) | 7609 (3) | 54(1) |
| O(2W) | 10828 (5) | 8138 (7) | 5099 (3) | 62(1) |

*Equivalent isotropic U defined as one third of the trace of the orthogonalized $U_{ij}$ tensor

*Equivalent isotropic U defined as one third of the trace of the orthogonalized $U_{ij}$ tensor

TABLE III

Bond Lengths (Å)

| | | | |
|---|---|---|---|
| C(1')−O(1A') | 1.262(7) | C(1')−O(1B') | 1.229(7) |
| (C1')−C(2') | 1.525(7) | C(2')−O(2') | 1.4347(6) |
| C(2')−C(3') | 1.500(9) | C(3')−O(3') | 1.416(8) |
| C(3')−C(4') | 1.526(7) | C(4')−O(4A') | 1.277(8) |
| C(4')−O(4B') | 1.201(8) | N(1)−N(2) | 1.402(5) |
| N(1)−C(5) | 1.278(7) | N(2)−C(2A) | 1.443(7) |
| N(2)−C(3) | 1.350(7) | C(3)−O(3) | 1.196(7) |
| C(3)−C(4) | 1.541(7) | C(4)−C(5) | 1.478(7) |
| C(4)−C(6) | 1.526(7) | C(4)−C(10) | 1.544(9) |
| C(5)−C(9) | 1.465(7) | C(6)−N(7) | 1.481(7) |
| N(7)−C(8) | 1.501(7) | C(8)−C(9) | 1.524(10) |
| C(10)−C(11) | 1.492(9) | C(11)−C(12) | 1.355(9) |
| C(11)−C(16) | 1.380(9) | C(12)−C(13) | 1.411(12) |
| C(13)−C(14) | 1.365(9) | C(14)−C(15) | 1.327(10) |
| C(15)−C(16) | 1.393(11) | | |

TABLE IV

Bond Angles (°)

| | | | |
|---|---|---|---|
| O(1A')−C(1')−O(1B') | 125.8(5) | O(1A')−C(1')−C(2') | 114.1(5) |
| O(1B')−C(1')−C(2') | 120.2(5) | C(1')−C(2')−O(2') | 109.8(4) |
| C(1')−C(2')−C(3') | 111.7(5) | O(2')−C(2')−C(3') | 109.7(5) |
| C(2')−C(3')−O(3') | 111.9(4) | C(2')−C(3')−C(4') | 110.7(5) |
| O(3')−C(3')−C(4') | 106.9(5) | C(3')−C(4')−O(4A') | 114.6(5) |
| C(3')−C(4')−O(4B') | 120.7(6) | O(4A')−C(4')−O(4B') | 124.6(5) |
| N(2)−N(1)−C(5) | 107.4(3) | N(1)−N(2)−C(2A) | 118.7(4) |
| N(1)−N(2)−C(3) | 113.8(4) | C(2A)−N(2)−C(3) | 127.5(5) |
| N(2)−C(3)−O(3) | 126.6(5) | N(2)−C(3)−C(4) | 104.3(4) |
| O(3)−C(3)−C(4) | 129.0(5) | C(3)−C(4)−C(5) | 100.9(4) |
| C(3)−C(4)−C(6) | 110.4(5) | C(5)−C(4)−C(6) | 109.6(5) |
| C(3)−C(4)−C(10) | 108.2(5) | C(5)−C(4)−C(10) | 114.0(5) |
| C(6)−C(4)−C(10) | 113.0(4) | N(1)−C(5)−C(4) | 113.4(4) |
| N(1)−C(5)−C(9) | 126.2(4) | C(4)−C(5)−C(9) | 119.5(4) |
| C(4)−C(6)−N(7) | 109.4(5) | C(6)−N(7)−C(8) | 115.0(4) |
| N(7)−C(8)−C(9) | 110.7(5) | C(5)−C(9)−C(8) | 108.4(5) |
| C(4)−C(10)−C(11) | 114.5(4) | C(10)−C(11)−C(12) | 120.2(5) |
| C(10)−C(11)−C(16) | 121.6(6) | C(12)−C(11)−C(16) | 118.3(7) |
| C(11)−C(12)−C(13) | 122.0(6) | C(12)−C(13)−C(14) | 115.9(7) |
| C(13)−C(14)−C(15) | 124.7(8) | C(14)−C(15)−C(16) | 117.8(6) |
| C(11)−C(16)−C(15) | 121.2(6) | | |

TABLE V

Anisotropic displacement coefficients (Å² × 10³)

| | $U_{11}$ | $U_{22}$ | $U_{33}$ | $U_{12}$ | $U_{13}$ | $U_{23}$ |
|---|---|---|---|---|---|---|
| C(1') | 32 (1) | 26 (1) | 34(1) | 2 (1) | 5 (1) | −8 (1) |
| O(1A') | 35 (1) | 19 (1) | 67(1) | −4 (1) | 2 (1) | 2 (1) |
| O(1B') | 35 (1) | 26 (1) | 60(1) | −4 (1) | −2 (1) | −13 (1) |
| C(2') | 32 (1) | 17 (1) | 36(1) | 1 (1) | −1 (1) | 1 (1) |
| O(2') | 32 (1) | 33 (1) | 43(1) | 4 (1) | −1 (1) | 0 (1) |
| C(3') | 41 (1) | 18 (1) | 37(1) | 6 (1) | 6 (1) | −6 (1) |
| O(3') | 71 (1) | 33 (1) | 41(1) | −2 (1) | 23 (1) | 1 (1) |
| C(4') | 28 (1) | 27 (1) | 39(1) | 2 (1) | 3 (1) | 2 (1) |
| O(4A') | 41 (1) | 32 (1) | 45(1) | −7 (1) | 10 (1) | −9 (1) |
| O(4B') | 56 (1) | 35 (1) | 92(1) | 7 (1) | 32 (1) | −2 (1) |
| N(1) | 39 (1) | 48 (1) | 37(1) | 4 (1) | −6 (1) | 7 (1) |
| N(2) | 30 (1) | 39 (1) | 47(1) | 2 (1) | −2 (1) | −4 (1) |
| C(2A) | 27 (1) | 66 (1) | 68(1) | −3 (1) | −2 (1) | −1 (1) |
| C(3) | 39 (1) | 40 (1) | 30(1) | 8 (1) | 10 (1) | −7 (1) |
| O(3) | 45 (1) | 27 (1) | 65(1) | −3 (1) | 5 (1) | 1 (1) |
| C(4) | 23 (1) | 34 (1) | 26(1) | 0 (1) | 2 (1) | 3 (1) |
| C(5) | 31 (1) | 32 (1) | 36(1) | −1 (1) | 6 (1) | 0 (1) |
| C(6) | 38 (1) | 38 (1) | 38(1) | 4 (1) | 1 (1) | −4 (1) |
| N(7) | 39 (1) | 42 (1) | 34(1) | 1 (1) | −6 (1) | −1 (1) |
| C(8) | 44 (1) | 46 (1) | 54(1) | −1 (1) | 1 (1) | −9 (1) |
| C(9) | 41 (1) | 42 (1) | 52(1) | 6 (1) | 2 (1) | 0 (1) |
| C(10) | 37 (1) | 46 (1) | 29(1) | 6 (1) | 9 (1) | 4 (1) |

TABLE V-continued

Anisotropic displacement coefficients ($\text{Å}^2 \times 10^3$)

| | $U_{11}$ | $U_{22}$ | $U_{33}$ | $U_{12}$ | $U_{13}$ | $U_{23}$ |
|---|---|---|---|---|---|---|
| C(11) | 39 (1) | 55 (1) | 37(1) | 10 (1) | 7 (1) | −2 (1) |
| C(12) | 72 (1) | 85 (1) | 49(1) | 4 (1) | 2 (1) | 1 (1) |
| C(13) | 103 (1) | 108 (1) | 82(1) | 2 (1) | 16 (1) | 27 (1) |
| C(14) | 103 (1) | 108 (1) | 73(1) | 13 (1) | 4 (1) | 6 (1) |
| C(15) | 81 (1) | 93 (1) | 63(1) | −4 (1) | −6 (1) | −17 (1) |
| C(16) | 80 (1) | 88 (1) | 58(1) | −4 (1) | 13 (1) | −12 (1) |
| O(1W) | 56 (1) | 45 (1) | 60(1) | −7 (1) | 7 (1) | −2 (1) |
| O(2W) | 58 (1) | 48 (1) | 91(1) | 3 (1) | 42 (1) | 7 (1) |

The anisotropic displacement exponent takes the form:

$$-2\pi^2(h^2 a^{*2} U_{11} + \ldots + 2hka^*b^* U_{12})$$

TABLE VI

H-Atom coordinates (×$10^4$) and isotropic displacement coefficients ($\text{Å}^2 \times 10^3$)

| | x | y | z | U |
|---|---|---|---|---|
| H(2') | 6314 | 9385 | 6665 | 80 |
| H(2A') | 8195 (10) | 8867 (10) | 7105 (9) | 50 |
| H(3') | 5656 | 9704 | 5398 | 80 |
| H(3A') | 8259 (10) | 11720 (10) | 5037 (9) | 50 |
| H(4A') | 5234 (10) | 6488 (10) | 6270 (9) | 50 |
| H(2A) | 2319 | 5061 | 1512 | 80 |
| H(2B) | 2495 | 6907 | 1046 | 80 |
| H(2C) | 1928 | 7053 | 1829 | 80 |
| H(6A) | 7999 | 4642 | 3381 | 80 |
| H(6B) | 6562 | 5972 | 3533 | 80 |
| H(7A) | 9771 (10) | 7980 (10) | 3431 (9) | 50 |
| H(7B) | 9183 (10) | 7721 (10) | 4160 (9) | 50 |
| H(8A) | 7229 | 9605 | 3689 | 80 |
| H(8B) | 9033 | 10220 | 3630 | 80 |
| H(9A) | 8599 | 9685 | 2362 | 80 |
| H(9B) | 7101 | 10908 | 2520 | 80 |
| H(10A) | 8417 | 4095 | 2071 | 80 |
| H(10B) | 9315 | 6067 | 2166 | 80 |
| H(12) | 9152 | 8192 | 1169 | 80 |
| H(13) | 8559 | 8747 | −149 | 80 |
| H(14) | 6799 | 6628 | −864 | 80 |
| H(15) | 5710 | 4049 | −375 | 80 |
| H(16) | 6471 | 3406 | 915 | 80 |
| H(1WA) | 8471 (10) | 5946 (10) | 7323 (9) | 52(1) |
| H(1WB) | 6863 (10) | 5969 (10) | 7529 (9) | 50 |
| H(2WA) | 11347 (10) | 8095 (10) | 5456 (9) | 50 |
| H(2WB) | 11515 (10) | 9176 (10) | 4829 (9) | 50 |

Preparation One
Step A. 4-oxo-Piperidine-1,3-dicarboxylic Acid 1-tert-Butyl Ester 3-Methyl Ester.

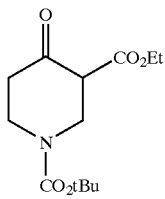

To a mixture of 7.00 g (36.2 mmol) of 4-oxo-piperidine-3-carboxylic acid methyl ester and 8.82 g (72.3 mmol) of 4,4-dimethylaminopyridine in 200 mL of methylene chloride at about 0° C. was added a solution of 7.88 g (36.2 mmol) of di-tert-butyldicarbonate in 150 mL of methylene chloride over about 30 min. The mixture was warmed to room temperature and then stirred for about 17 h. The mixture was concentrated and the residue was diluted with chloroform and washed three times each with 10% aqueous HCl, saturated aqueous sodium bicarbonate solution and brine, dried over $MgSO_4$ and concentrated to give 9.18 g of a clear yellow oil.

Step B. 3-(R,S)-Benzyl-4-oxo-piperidine-1,3-dicarboxylic Acid 1-tert-Butyl Ester 3-Methyl Ester.

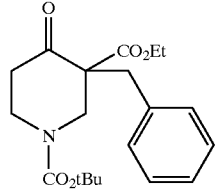

To a solution of the compound prepared according to Step A (5.00 g, 19.4 mmol) in 10 mL of DMF was added 745 mg (7.4 mmol) of sodium hydride (60% oil dispersion) and the mixture was stirred at room temperature for about 15 min. A solution of 3.32 g (19.4 mmol) benzylbromide in 15 mL of DMF was added to the stirring solution by cannula and the mixture was stirred for about 42 h at room temperature. The mixture was diluted with ethyl acetate and washed once with water and four times with brine, dried over $MgSO_4$, and concentrated to give 6.0 g of the title compound of Step B as a yellow oil. MS (Cl, $NH_3$) 348 ($MH^+$).

Step C. 3a-(R,S)-Benzyl-2-methyl-3-oxo-2,3,3a,4,6,7-hexahydro-pyrazolo[4,3-c]-pyridine-5-carboxylic Acid tert-Butyl Ester.

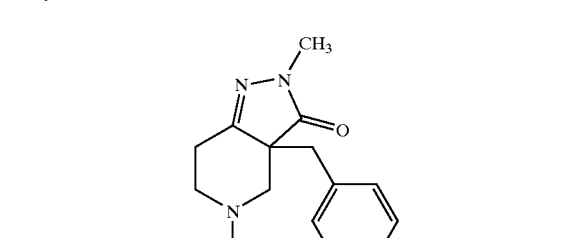

A mixture of the compound prepared according to Step B (4.00 g, 11.5 mmol) and 530 mg (11.5 mmol) of methylhydrazine in 100 mL of ethanol was heated at reflux for about 8 h. The mixture was concentrated and the residue was dissolved in 100 mL toluene and heated at reflux for about 17 h. The mixture was concentrated and the residue was purified by silica gel chromatography using an elution gradient of (15:85 v/v ethyl acetate:hexane) to (75:25 v/v ethyl acetate:hexane) to give 2.6 g of the title compound of Step C as a clear colorless oil. MS (Cl, $NH_3$) 344 ($MH^+$).

Step D. 3a(R)-Benzyl-2-methyl-2,3,3a,4,6,7-hexahydro-pyrazolo[4,3-c]pyridin-3-one (L)-Tartrate.

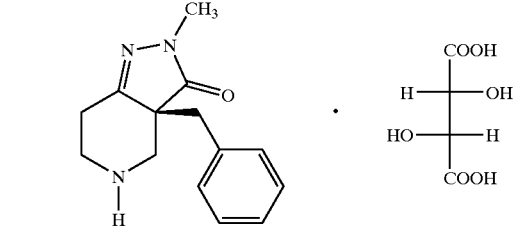

To a 2 liter, round bottom flask, equipped with a mechanical stirrer, addition funnel, and a thermocouple was added, sequentially, 3a-(R,S)-benzyl-2-methyl-3-oxo-2,3,3a,4,6,7- hexahydro-pyrazolo[4,3-c]-pyridine-5-carboxylic acid tert-butyl ester (prepared according to Step C, 51.5 g, 0.15 moles, 1.0 equivalents) and methylene chloride (515 ml, 10 volumes). The mixture was agitated to form a solution which was then cooled to an internal temperature of 0° C.–5° C. To the cooled mixture was added trifluoroacetic acid (TFA, 130 ml, 192 g, 1.68 moles, 11.2 eq., 2.5 volumes). The TFA was added via the addition funnel over 15 minutes while maintaining an internal temperature of 0° C.–5° C. The reaction mixture was warmed to about 20° C. over 3 hours and then the reaction mixture was cooled to 10° C.–15° C. To the cooled reaction mixture was added sodium carbonate (92 g, 0.868 moles) in water (920 mL) over 20 minutes. The pH was 7.5. The reaction mixture was transferred to a 2 liter separatory funnel and allowed to settle. The organic portion was decanted and the aqueous portion was extracted with methylene chloride (130 ml, 2.5 volumes). The combined organic portions were transferred back to the 2 liter reactor and to it was added L-tartaric acid (24.77 g, 0.165 moles, 1.1 equivalents) dissolved in acetone (354 ml, about 7 volumes) and water (44 mL, about 1 volume). The reaction mixture was agitated and heated at about 38° C. overnight. The resultant slurry was cooled to 0° C.–5° C., granulated for 1 hour, then filtered. The solids were washed with 100 ml of cold acetone and then dried in vacuo at 40° C.–50° C. for 16 hours to afford 51.86 g (87.9% yield) of the title compound of Step D.

Preparation Two

Step A 4-oxo-3-Pyridin-2-yl-methyl-piperidine-1,3-dicarboxylic Acid 1-tert-Butyl Ester 3-Ethyl Ester.

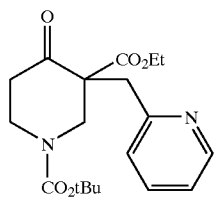

To a solution of 4-oxo-piperidine-1,3-dicarboxylic acid 1-tert-butyl ester 3-ethyl ester (prepared according to the method of Preparation One, Step A, 10.34 g, 38.2 mmol) in DMF (40 mL) at about 0° C. was added picolyl chloride hydrochloride (5.7 g, 34.7 mmol), potassium carbonate (14.4 g, 104.1 mmol) and potassium iodide (5.76 g, 34.7 mmol). After stirring at about 0° C. for about 2 hours, the ice bath was removed and DABCO (973 mg, 8.68 mmol) was added. The reaction mixture was stirred for about 30 min. and poured into a mixture of water and IPE. The organic layer was separated and washed with saturated aqueous NaHCO₃ and saturated aqueous NaCl, dried over Na₂SO₄ and concentrated in vacuo. The crude residue was crystallized from hexanes to give a white solid (8.19 g, yield 65%). $^1$H-NMR (CDCl₃) δ 1.17 (t, 3H), 1.48 (s, 9H), 1.55 (s, 2H), 2.61 (m, 1H), 2.71 (m, 1H), 3.31–3.50 (m, 3H), 4.11 (d, 2H), 4.49 (d, 1H), 7.06 (br, s, 1H), 7.17 (d, 1H), 7.54 (m, 1H), 8.40 (s, 1H).

Step B. 3-oxo-3a-Pyridin-2-ylmethyl-2-(2,2,2-trifluoro-ethyl)-2,3,3a,4,6,7-hexahydro-pyrazolo[4,3-c]pyridine-5-carboxylic Acid tert-Butyl Ester.

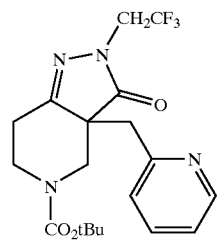

A 70% aqueous solution of CF₃CH₂NHNH₂ (325 mL, 1.986 mol) was extracted with toluene (3×1200 mL). To a solution of the compound prepared according to step A (600 g, 1.655 mol) in toluene (900 mL) was first added the combined toluene extracts containing the anhydrous 2,2,2-trifluoroethyl hydrazine, followed by acetic acid (121.4 g, 1.986 mol). The reaction mixture was heated at about 70° C. for about 2 hours, then another toluene extraction of 70% aqueous 2,2,2-trifluoroethyl hydrazine (50 g) was added. The reaction mixture was heated at about 80° C. for about 3.5 hours, cooled to room temperature and diluted with saturated aqueous NaHCO₃ (2 L). The toluene layer was separated and washed with saturated aqueous NaCl, dried over Na₂SO₄ and concentrated in vacuo to give an oil (754.8 g). Crystallization from methanol/water afforded the desired product as a white solid (609.5 g). $^1$H-NMR (CDCl₃) δ 1.50 (s, 9H), 2.53 (d, 1H), 2.70 (br, s, 2H), 2.88 (br, s, 1H), 3.31 (m, 2H), 3.97 (m, 1H), 4.19 (m, 1H), 4.46 (br, s, 1H), 4.63 (br, s, 1H), 7.06 (m, 2H), 7.51(m, 1H), 8.34 (m, 1H).

Step C. 3a-Pyridin-2-yl-methyl-2-(2,2,2-trifluoroethyl)-2,3a,4,5,6,7-hexahydro-pyrazolo[4,3-c]pyridin-3-one.

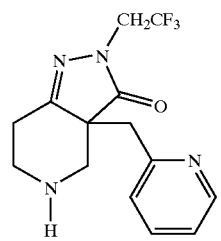

Methanesulfonic acid (11.6 g, 121 mmol) was added dropwise to a solution of the compound prepared according to step B (10 g, 24.2 mmol) in CH₂Cl₂ (100 mL) over about 30 minutes. The reaction mixture was stirred for about 1 hour, then cooled to about 0° C., and then triethylamine (18.6 mL, 133.1 mmol) was added through an addition funnel. The mixture was allowed to warm to room temperature over about 1 hour, diluted with additional CH₂Cl₂ and washed with saturated aqueous NaCl, dried over Na₂SO₄, filtered and concentrated in vacuo to afford the product as a white solid (7.2 g). $^1$H-NMR (CDCl₃) δ: 2.51–2.72 (m, 4H), 3.35 (m, 2H), 3.49 (m, 2H), 4.03 (m, 1H), 4.25 (m, 1H), 7.08 (d, 2H), 7.51 (t, 1H), 8.37 (d, 1H).

Step D. 3a-Pyridin-2-ylmethyl-2-(2,2,2-trifluoroethyl)-2,3a,4,5,6,7-hexahydro-pyrazolo[4,3-c]pyridin-3-one (D)-Tartrate.

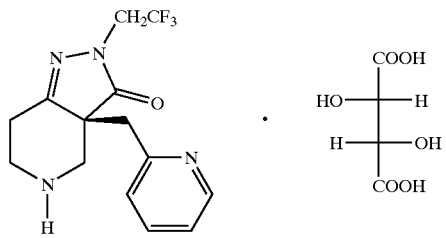

In a dry and nitrogen purged 5 L round bottom flask equipped with a mechanical stirrer, D-(−) tartaric acid (129 g, 0.86 mol) was added to the compound prepared according to step C (243 g, 0.78 mol) in acetone/water (9:1, 2430 mL) at about 17° C. The mixture was stirred at room temperature overnight, filtered, the solid was collected and washed with cold acetone and dried under vacuum. The product was obtained as a yellow solid (284 g, yield 78.8%).

Preparation Three
Step A. 2-tert-Butoxycarbonylamino-2-methyl-propionic Acid 2,5-Dioxo-pyrrolidin-1-yl Ester.

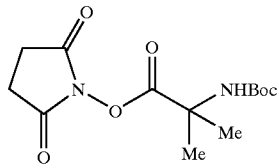

A stirred solution of N-hydroxysuccinimide (112 g, 0.973 mol), N-t-butoxycarbonyl-α-methylalanine (197 g, 0.969 mol), and 1-(3-dimethylaminopropyl)-3-ethyl-carbodiimide (186 g, 0.970 mol) in anhydrous dichloromethane (1.4 L) was stirred at room temperature for about 18 hours under nitrogen atmosphere. The reaction mixture was washed three times each with saturated sodium bicarbonate solution and then brine. The organic layer was dried over sodium sulfate, filtered and concentrated in vacuo to give the title compound of Step A as a white solid (256 g, 88%): PBMS (M+18)$^+$318; $^1$H NMR=250 MHz (CDCl$_3$) δ :4.91 (N$\underline{H}$, br, s, 1H), 2.84 (—CO(C$\underline{H}_2$)$_2$CO—, s, 4H), 1.67 (Me, s, 6H), 1.48 (BOC, s, 9H).

Step B. 2(R)-3-Benzyloxy-2-(2-tert-butoxycarbonylamino-2-methyl-propionylamino)-propionic Acid.

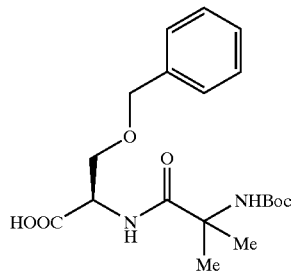

To a solution of D-O-benzylserine (106 g, 0.532 mol) and the title compound of Step A (160 g, 0.532 mol) in water/dioxane (250/1000 mL) was slowly added triethylamine (223 mL, 1.60 mol) at room temperature. The reaction was heated to about 50° C. and stirred for about 15 hours under nitrogen atmosphere. The solvent was then removed in vacuo, ethyl acetate was added, and the stirred mixture was acidified with 10% aqueous HCl solution to pH 2–3. The organic layer was dried over sodium sulfate, filtered and concentrated in vacuo to give the title compound of Step B (200 g, 99%): -Apcl MS (M−1)$^-$ 379; $^1$H NMR=300 MHz (methanol-d$_4$) δ :7.69 (N$\underline{H}$, d, 1H), 7.32 (Ph, m, 5H), 4.60 (C$\underline{H}$CO$_2$H, m, 1H), 4.51 (C$\underline{H}_2$Ph, s, 2H), 3.81 (C$\underline{H}_2$Obz, m, 2H), 1.41 (Me, s, 6H), 1.40 (BOC, s, 9H).

Preparation Four

Step A 2(R)-2-tert-Butoxycarbonylamino-3-(2,4-difluoro-benzyloxy)-propionic Acid.

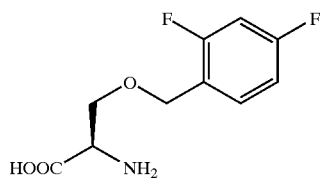

To a solution of N-Boc-(D)-serine (452 g, 2.2026 mol) in a mixture of THF (7 L) and DMF (3 L) at about 0° C. was added potassium tert-butoxide solution (515.8 g, 4.5963 mol). The reaction mixture was stirred at about 0° C. for about 30 min., then 2,4-difluorobenzyl bromide (456.5 g, 2.2051 mol) was added. After warming to room temperature, the reaction mixture was concentrated in vacuo to remove the THF. The reaction mixture was partitioned between 4.5 L H$_2$O and 4.5 L IPE. The layers were separated and the pH of the aqueous layer was adjusted with 1 N HCl to about 3. The aqueous layer was extracted twice with 4 L each of IPE. The organic solution was dried over Na$_2$SO$_4$, and concentrated in vacuo to yield a yellow waxy solid (518.0 g, yield: 70.9%). $^1$H-NMR (CDCl$_3$) δ 1.44 (s, 9H), 3.73 (m, 1H), 3.94 (d, 1H), 4.44 (br, s, 1H), 4.54 (s, 2H), 5.34 (m, 1H), 6.78 (m, 1H), 6.84 (m, 1H), 7.30 (m, 1H).

Step B. 2(R)-2-Amino-3-(2,4-difluoro-benzyloxy)-propionic Acid, Methanesulfonic Acid Salt.

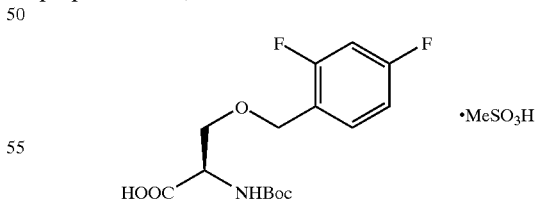

To a solution of the product from Step A (1.19 g, 3.59 mmol) in CH$_2$Cl$_2$/IPE (1:1, 12 mL) was added methanesulfonic acid (1.72 g, 17.95 mmol) through a syringe over about 10 minutes. A solid immediately precipitated out of solution. After about 1 hour, the solid was filtered and washed with a CH$_2$Cl$_2$/IPE mixture (1:1) to afford 939 mg of product (yield 80%).

Step C. 2(R)-2-(2-tert-Butoxycarbonylamino-2-methyl-propionylamino)-3-(2,4-difluoro-benzyloxy)-propionic Acid.

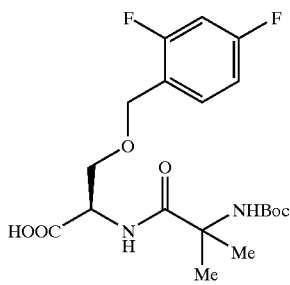

To a solution of the product from Step B (520 mg, 1.46 mmol) in THF/water (4:1, 10 mL) was added 2-tert-butoxycarbonylamino-2-methyl-propionic acid-2,5-dioxo-pyrrolidin-1-yl ester (438 mg, 1.46 mmol) and triethylamine (369 mg, 3.65 mmol). The reaction mixture was stirred at room temperature for about 1 hour and quenched with a 10% aqueous citric acid solution (10 mL). After about 15 min., ethyl acetate (50 mL) was added and the organic layer was separated and washed with saturated aqueous NaCl, dried over $Na_2SO_4$ and concentrated in vacuo to give a foam (534.1 mg, yield 88%). $^1$H-NMR ($CD_3OD$): 61.38 (br, s, 15H), 3.77 (d, 1H), 3.92 (d, 1H), 4.52 (m, 3H), 6.92 (m, 1H), 7.41 (m, 1H), 7.58 (d, 1H).

Preparation Five (3aR)-2,3a,4,5,6,7-Hexahydro-2-methyl-3a-(Phenylmethyl)-3H-pyrazolo[4,3-c]pyridin-3-one, (2R,3R)-2,3-Dihydroxybutanedioate (1:1)

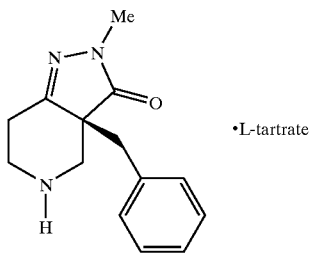

Step A: 4-oxo-1-(Phenylmethyl)-3-piperidinecarboxylic Acid Methyl Ester, Hydrochloride.

A solution of 1-benzyl4-piperidone (56.5 kg, 1.0 eq.) in toluene (189 L) was prepared at 15° C. to 25° C. A second reactor was charged with toluene (659 L), potassium tert-butoxide (71.9 kg, 2.25 eq.) and dimethyl carbonate (51.5 kg, 2.0 eq.) at 15° C. to 25° C. The resulting slurry was warmed to a temperature of 80° C. to 90° C. The solution of 1-benzyl-4-piperidone in toluene was added slowly to the slurry over 60 to 90 minutes. After an additional 90 minutes, the reaction mixture was cooled to below 15° C. The completed reaction was quenched with acetic acid (38.5 kg, 2.25 eq.) and water (367 L). The two phase mixture was separated. The organic layer was filtered to remove solids. The organic filtrate was concentrated by distillation under reduced pressure to a volume of approximately 150 L. Toluene (799 L) was added to the concentrated mixture. Addition of hydrogen chloride (gas, 11.0 kg, 1.05 eq.) afforded the hydrochloride salt as a precipitate. The slurry was stirred at 10° C. to 15° C. for 30 minutes. The solids were isolated by filtration, washed with approximately hexanes (130 L), and dried using vacuum to give 79.4 kg of 4-oxo-1-(phenylmethyl)-3-piperidinecarboxylic acid methyl ester, hydrochloride (97.8% yield). Analysis calculated for $C_{14}H_{17}NO_3.HCl$: C 59.3; H 6.39; N 4.94; found: C 59.7H, 6.65 N, 4.85.

Step B: 4-oxo-1-Piperidinecarboxylic Acid Methyl ester, Hydrochloride.

Into a clean, dry, nitrogen purged reactor was added 4-oxo-1-(phenylmethyl)-3-piperidinecarboxylic acid methyl ester, hydrochloride (prepared according to Preparation Five, Step A, 78.8 kg, 1.0 eq.), ethanol (416 L), water (340 L), and 10% palladium on carbon (catalyst, 7.88 kg, 0.1 kg/kg). The mixture was subjected to hydrogenation conditions of approximately 45 psig ($32 \times 10^3$ kg/m$^2$) of hydrogen pressure at a temperature between 25° C. to 35° C. for approximately 18 hours. After the reaction was complete, the reaction mixture was vented with nitrogen and filtered to removed the spent catalyst. The catalyst cake was washed with ethanol (150 L). The filtrate and washes were concentrated under reduced pressure to approximately 57 L. The product was crystallized by the slow addition of 2-propanol (227 L). The slurry was cooled to 10° C. to 20° C. and stirred for approximately one hour. The product was isolated by filtration, rinsed with hexanes (76 L), and dried under vacuum for approximately 24 hours to give 43.2 kg 4-oxo-1-piperidinecarboxylic acid methyl ester, hydrochloride (80.0% yield). Analysis calculated for $C_7H_{11}NO_3.HCl$: C 43.42; H 6.25; N 7.23; found: C 43.7; H 6.59; N 7.19.

Step C: 4-oxo-1,3-Piperidinecarboxylic Acid 1-(1,1-Dimethylethyl) 3-Methyl Ester.

A clean, dry, nitrogen purged, glass-lined vessel was charged with isopropyl ether (IPE, 309 L), 4-oxo-1-piperidinecarboxylic acid methyl ester, hydrochloride (prepared according to Preparation Five, Step B, 42.6 kg, 1.0 eq.), and water (153 L) at 15 to 25° C. Addition of triethylamine (28.9 kg, 1.3 eq.) resulted in a thick white emulsion. Slow addition of di-tert-butyldicarbonate (52.6 Kg, 50 L, 1.1 eq.) to the reaction mixture, followed by an IPE rinse, resulted in a clear biphasic solution. The mixture was agitated at 15° C. to 25° C. for about 12 hours. After reaction completion, the aqueous layer was separated off and extracted with IPE (20 L). The organic extracts were combined and washed sequentially with 1N HCl (110 L), water (90 L), and saturated sodium chloride solution (103 L). The washed organic layer was dried over anhydrous sodium sulfate. The mixture was filtered to remove insolubles. The filtrate was concentrated using vacuum distillation to give the oil 4-oxo-1,3-piperidinedicarboxylic acid 1-(1,1-dimethylethyl) 3-methyl ester. About 49 L (53 kg) of product oil (assumed 95% yield) was collected. The oil was held in the reactor for immediate use in the next step.

Step D: 4-oxo-3-(Phenylmethyl)-1,3-piperidinedicarboxylic Acid 1-(1,1-Dimethylethyl) 3-Methyl Ester.

The nitrogen purged vessel containing about 4-oxo-1,3-piperidinedicarboxylic acid 1-(1,1-dimethylethyl) 3-methyl ester (prepared according to Preparation Five, Step C, 53 kg, 49 L, 1.0 eq.) was charged with tetrahydrofuran (THF, 536 L) and potassium carbonate (72 kg, 2.5 eq.). The slurry was treated with benzyl bromide (36.0 kg, 1.01 eq.) over 10 to 15 minutes. The reaction mixture was heated at reflux temperature until reaction was complete (generally between 12 and 18 hours). The mixture was cooled to between 20° C. and 25° C., filtered to remove the salts, and the filter cake washed with THF (134 L). The THF was removed from the mixture by partial vacuum distillation and replaced with heptanes (402 L). The resulting slurry was cooled to between −5° C. and 5° C. and stirred for about one hour. The solids were collected by filtration, washed with heptanes (57 L) cooled between 0° C. to 10° C., and dried under vacuum between 45° C. to 55° C. to give 50.1 kg of 4-oxo-3-(phenylmethyl)-1,3-piperidinedicarboxylic acid 1-(1,1-dimethylethyl) 3-methyl ester (69.2% yield). HPLC assay showed a product peak of 99.2% at about 12 minutes. HPLC conditions: Intersil C-8 column, 4.6×150 mm; mobile phase: 50%acetonitrile/water; aqueous phase: 1 L water, 3 mL triethylamine and 1 mL $H_3PO_4$ at pH 6.5; flow rate 1.0 mL/min.; detected by UV at 210 nm.

Step E: 2,3,3a,4,6,7-Hexahydro-2-methyl-3-oxo-3a-(Dhenylmethyl)-5H-pyrazolo[4,3-c]pyridine-5-carboxylic Acid 1,1-Dimethylethyl Ester.

Methylhydrazine is highly toxic, is a cancer suspect agent, is flammable and is potentially explosive. It should be handled with extreme care. Have spill kits, drying agents, liqua paks and fire extinguishers on hand during handling. Ensure air hoses are long enough to escape any accident scene. Since methylhydrazine can react with metal oxides, the reaction vessel was inspected to ensure that no metal surfaces were exposed prior to initiating the reaction. In a clean, glass-lined, nitrogen purged vessel, 4-oxo-3-(phenylmethyl)-1,3-piperidinedicarboxylic acid 1-(1,1-dimethylethyl) 3-methyl ester (prepared according to Preparation Five, Step D, 50.1 kg, 1.0 eq.) was dissolved in methyl-t-butyl ether (MTBE, 208 L) at 15° C. to 20° C. to form a solution. The reaction solution was charged with methylhydrazine (7.6 kg, 1.15 eq.). After stirring for about 30 minutes, acetic acid (13.0 kg, 1.5 eq.) was added. The reaction mixture was slowly heated to reflux temperature (53° C. to 57° C.) and held at reflux for 15 to 20 hours. The reaction was cooled to between 20° C. and 25° C. The reaction mixture was cooled to between 5° C. and 10° C. and slowly charged with 10% sodium bicarbonate solution in water (175 L). The biphasic mixture was separated and the organic layer was washed sequentially with water (175 L) and saturated sodium chloride solution (175 L). The aqueous wash layers should be combined and treated with bleach solution to destroy any residual methylhydrazine prior to disposal. The organic solution was concentrated to a volume between 130 and 170 L under partial vacuum. Addition of heptanes (174 L) to the mixture precipitated the product. The slurry was stirred for 2 hours at a temperature between 5° C. and 10C. The solids were isolated by filtration, washed with cold MTBE (34 L), and dried under vacuum at a temperature between 35° C. and 45° C. for 24 hours to give 47.1 kg of 2,3,3a,4,6,7-hexahydro-2-methyl-3-oxo-3a-(phenylmethyl)-5H-pyrazolo[4,3-c]pyridine-5-carboxylic acid 1,1-dimethylethyl ester (95.1% yield). HPLC assay showed a product peak of 99.1% at about 5 minutes. HPLC conditions: Intersil C-8 column, 4.6×150 mm; mobile phase: 50%acetonitrile/water; aqueous phase: 1 L water, 3 mL triethylamine and 1 mL $H_3PO_4$ at pH 6.5; flow rate 1.0 mL/min.; detected by UV at 205 nm.

Step F: (3aR)-2,3a,4,5,6,7-Hexahydro-2-methyl-3a-(phenylmethyl)-3H-pyrazolo[4,3-c]pyridin-3-one, (2R,3R)-2,3-Dihydroxybutanedioate (1:1).

It has been observed that the intermediate free amine epimerizes in solution and as an isolated solid. Therefore, the dynamic resolution step was completed immediately following the deprotection step. A clean, nitrogen purged reactor was charged with methylene chloride (471 L) and 2,3,3a,4,6,7-hexahydro-2-methyl-3-oxo-3a-(phenylmethyl)-5H-pyrazolo[4,3-c]pyridine-5-carboxylic acid 1,1-dimethylethyl ester (prepared according to Preparation Five, Step E, 47.0 kg, 1.0 eq.). The mixture was agitated and cooled to between −5° C. and 5° C. The reaction mixture was slowly charged with triflouroacetic acid (117 kg, 7.5 eq.). The reaction mixture was warmed to a temperature between 20° C. and 30° C. and stirred for 12 to 15 hours. The reaction mixture was quenched by slow addition of an aqueous solution of 10% sodium carbonate (486 L, 0.5 eq.) at a temperature between 5° C. and 15° C. The organic layer was separated and the aqueous layer extracted with methylene chloride (19 L).

A mixture of acetone (456 L), water (56.4 L), and L-tartaric acid (22.6 kg, 1.1 eq.) was prepared in a second reactor. The tartaric acid mixture was combined with the organic layers at a temperature between 20° C. and 25° C. The resulting slurry was heated to a temperature between 35° C. and 45° C. and stirred for 8 to 18 hours (overnight). When the reaction was judged to be complete, the slurry was cooled and granulated at a temperature between 0° C. and 10° C. for three to four hours and filtered. The product cake was washed with a mixture of acetone (40 L) and water (4.5 L). The product was dried under vacuum using only mild heat (applied if evaporation of acetone results in cooling). A yield of 37.7 kg of (3aR)-2,3a,4,5,6,7-hexahydro-2-methyl-3a-(phenylmethyl)-3H-pyrazolo[4,3-c]pyridin-3-one, (2R, 3R)-2,3-dihydroxybutanedioate (1:1) was obtained (70.1% yield).

What is claimed is:

1. A process of preparing a compound of Formula II,

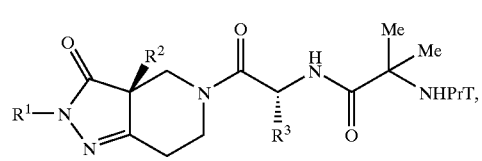

wherein:

$R^1$ is —$(C_1-C_{10})$alkyl optionally substituted with up to three fluoro atoms;

$R^2$ is phenylmethyl or 2-pyridylmethyl;

$R^3$ is —$(C_1-C_5)$alkyl-O—$(C_0-C_5)$alkylphenyl, where the phenyl substituent in the definition of $R^3$ is optionally substituted with up to three fluoro atoms; and Prt is an amine protecting group, comprising:

a) mixing an appropriate chiral tartrate salt having the structure of Formula IV,

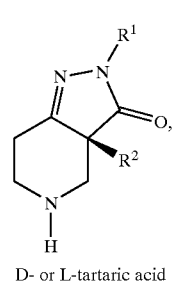

D- or L-tartaric acid wherein $R^1$ and $R^2$ are as defined above, and an organic amine in a reaction inert solvent at a temperature of about −68° C. to about −40° C. to form a slurry;

b) adding a compound of the Formula V,

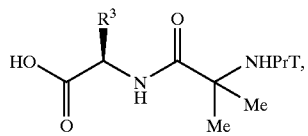

V wherein R³ and Prt are as defined above,
to said slurry to form a reaction mixture comprising the tartrate salt of the organic amine, the free base of a compound of Formula IV and a compound of the formula V; and c) adding a coupling reagent to said reaction mixture to form a compound of Formula II.

2. A process of claim 1 wherein said compound of Formula IV is suspended in said solvent prior to the addition of said organic amine.

3. A process of claim 2 wherein said slurry is warmed to about −50° C. prior to step b.

4. A process of claim 1 wherein: in step a, said organic amine is triethylamine; in step b, R³ is phenylmethyloxymethyl or 2,4-difluorophenylmethyloxymethyl and Prt is tert-butyloxycarbonyl; and in step c, said coupling reagent is propane phosphonic acid anhydride.

5. A process of claim 4 wherein $R^1$ is methyl or 2,2,2-trifluoroethyl and $R^2$ is phenylmethyl or 2-pyridylmethyl.

6. A process of claim 5 wherein the compound of Formula II selected from (1-(2-(1(R)-(2,4-difluorobenzyloxymethyl)-3a(R)-pyridin-2-ylmethyl-2-(2,2,2-trifluoro-ethyl)-3-oxo-2,3,3a,4,6,7-hexahydro-pyrazolo[4,3-c]pyridin-5-yl)-2-oxo-ethylcarbamoyl)-1-methyl-ethyl)-carbamic acid tert-butyl ester and (1-(2-(3a(R)-benzyl-2-methyl-3-oxo-2,3,3a,4,6,7-hexahydro-pyrazolo[4,3-c]pyridin-5-yl)-1(R)-benzyloxymethyl-2-oxo-ethylcarbamoyl)-1-methyl-ethyl)-carbamic acid tert-butyl ester is prepared.

7. A process of claim 5 wherein a compound of Formula IIA,

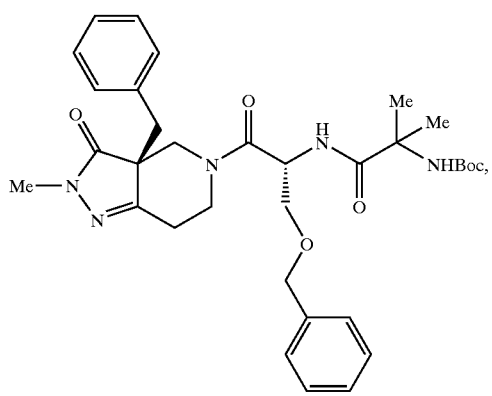

IIA wherein Boc is tert-butloxycarbonyl, is prepared.

8. A process of claim 5 wherein a compound of Formula IIB,

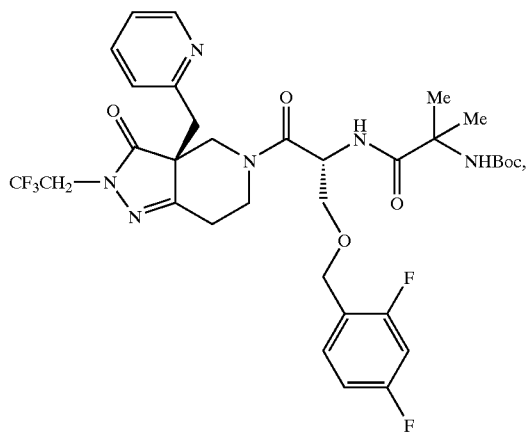

IIB wherein Boc is tert-butyloxycarbonyl, is prepared.

9. A process of claim 2 wherein: in step a, said organic amine is triethylamine; in step b, R³ is phenylmethyloxymethyl or 2,4-difluorophenylmethyloxymethyl and Prt is tert-butyloxycarbonyl; and in step c, said coupling reagent is propane phosphonic acid anhydride.

10. A process of claim 9 wherein $R^1$ is methyl or 2,2,2-trifluoroethyl and $R^2$ is phenylmethyl or 2-pyridylmethyl.

11. A process of claim 10 wherein the compound of Formula II selected from (1-(2-(1(R)-(2,4-difluorobenzyloxymethyl)-3a(R)-pyridin-2-ylmethyl-2-(2,2,2-trifluoro-ethyl)-3-oxo-2,3,3a,4,6,7-hexahydro-pyrazolo[4,3-c]pyridin-5-yl)-2-oxo-ethylcarbamoyl)-1-methyl-ethyl)-carbamic acid tert-butyl ester and (1-(2-(3a(R)-benzyl-2-methyl-3-oxo-2,3,3a,4,6,7-hexahydro-pyrazolo[4,3-c]pyridin-5-yl)-1(R)-benzyloxymethyl-2-oxo-ethylcarbamoyl)-1-methyl-ethyl)-carbamic acid tert-butyl ester is prepared.

12. A process of claim 10 wherein a compound of Formula IIA,

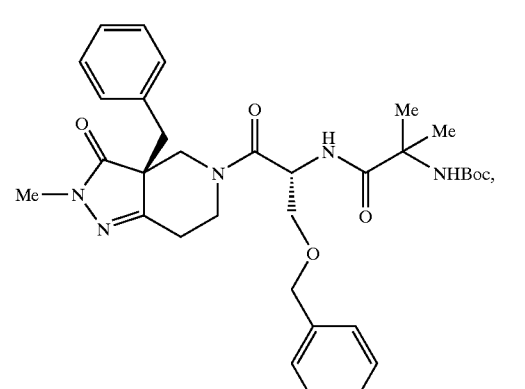

IIA wherein Boc is tert-butyloxycarbonyl, is prepared.

13. A process of claim 10 wherein a compound of Formula IIB,

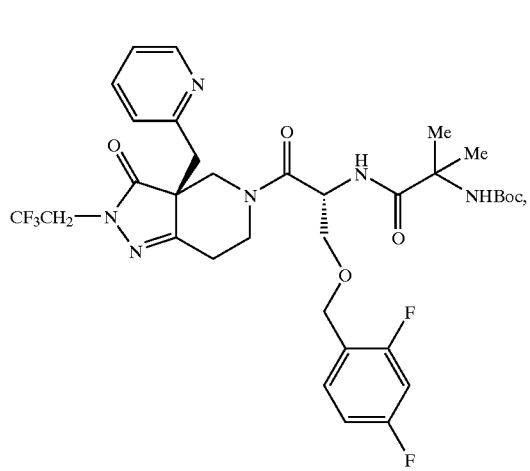

wherein Boc is tert-butyloxycarbonyl, is prepared.

14. A process of claim 3 wherein: in step a, said organic amine is triethylamine; in step b, R³ is phenylmethyloxymethyl or 2,4-difluorophenylmethyloxymethyl and Prt is tert-butyloxycarbonyl; and in step c, said coupling reagent is propane phosphonic acid anhydride.

15. A process of claim 14 wherein R¹ is methyl or 2,2,2-trifluoroethyl and R² is phenylmethyl or 2-pyridylmethyl.

16. A process of claim 15 wherein the compound of Formula II selected from (1-(2-(1(R)-(2,4-difluorobenzyloxymethyl)-3a(R)-pyridin-2-ylmethyl-2-(2,2,2-trifluoro-ethyl)-3-oxo-2,3,3a,4,6,7-hexahydro-pyrazolo[4,3-c]pyridin-5-yl)-2-oxo-ethylcarbamoyl)-1-methyl-ethyl)-carbamic acid tert-butyl ester and (1-(2-(3a(R)-benzyl-2-methyl-3-oxo-2,3,3a,4,6,7-hexahydro-pyrazolo[4,3-c]pyridin-5-yl)-1(R)-benzyloxymethyl-2-oxo-ethylcarbamoyl)-1-methyl-ethyl)-carbamic acid tert-butyl ester is prepared.

17. A process of claim 15 wherein a compound of Formula IIA,

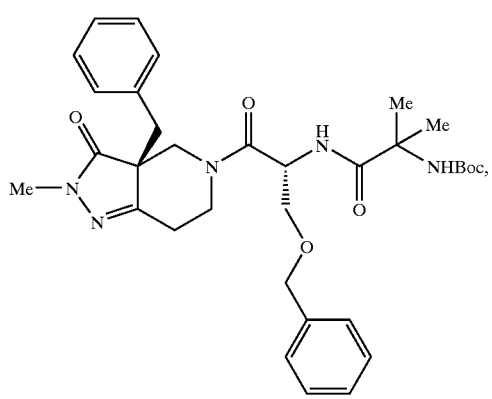

wherein Boc is tert-butyloxycarbonyl is prepared.

18. A process of claim 15 wherein a compound of Formula IIB,

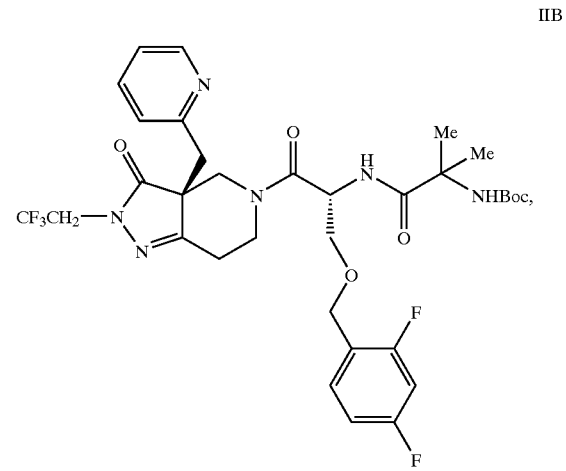

wherein Boc is tert-butyloxycarbonyl is prepared.

19. A process for preparing a compound of Formula III,

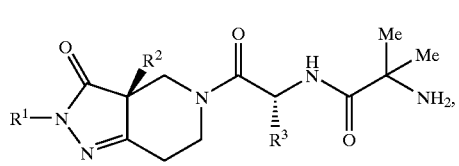

wherein:

R¹ is —(C₁–C₁₀)alkyl optionally substituted with up to three fluoro atoms;

R² is phenylmethyl or 2-pyridylmethyl; and

R³ is —(C₁–C₅)alkyl-O—(C₀–C₅)alkylphenyl, where the phenyl substituent in the definition of R³ is optionally substituted with up to three fluoro atoms, comprising:
  a) mixing an appropriate chiral tartrate salt having the structure of Formula IV,

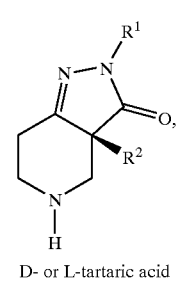

D- or L-tartaric acid wherein R¹ and R² are as defined above, and an organic amine in a reaction inert solvent at a temperature of about −68° C. to about −45° C. to form a slurry;

b) adding a compound of the Formula V,

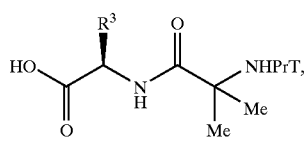

V wherein R³ is as defined above and Prt is an amine protecting group, to said slurry to form a reaction mixture comprising the tartrate salt of the organic amine, the free base of a compound of Formula IV and a compound of the Formula V;

c) adding a coupling reagent to said reaction mixture to form a compound of Formula II; and d) reacting said compound of Formula II with a suitable deprotecting reagent to form a compound of Formula III.

20. A process of claim 19 wherein said compound of Formula IV is suspended in said solvent prior to the addition of said organic amine comprising the additional step of warming said slurry to about −50° C. to about −40° C. prior to step b.

21. A process of claim 20 wherein said Prt is tert-butyloxycarbonyl and said tert-butyloxycarbonyl is removed by reacting said compound of Formula II with an acid.

22. A process of claim 21 wherein said acid is methanesulfonic acid.

23. A process of claim 22 wherein: R³ is phenylmethyloxymethyl or 2,4-difluorophenylmethyloxymethyl; in step b, said organic amine is triethylamine; and in step c, said coupling reagent is propane phosphonic acid anhydride.

24. A process of claim 23 wherein R¹ is methyl or 2,2,2-trifluoroethyl and R² is phenylmethyl or 2-pyridylmethyl.

25. A process of claim 24 wherein said compound of Formula III selected from 2-amino-N-[2-(3a(R)-benzyl-2-methyl-3-oxo-2,3,3a,4,6,7-hexahydro-pyrazolo-[4,3-c]pyridin-5-yl-1(R)-benzyloxylmethyl-2-oxo-ethyl]-isobutyramide and 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl-2-methyl-propionamide is prepared.

26. A process of claim 24 wherein a compound of formula IIIA,

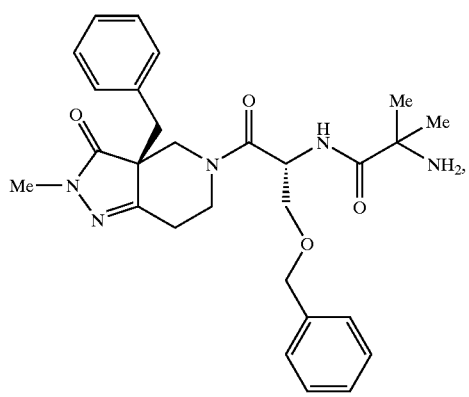

IIIA is prepared.

27. A process of claim 24 wherein a compound of formula IIIB,

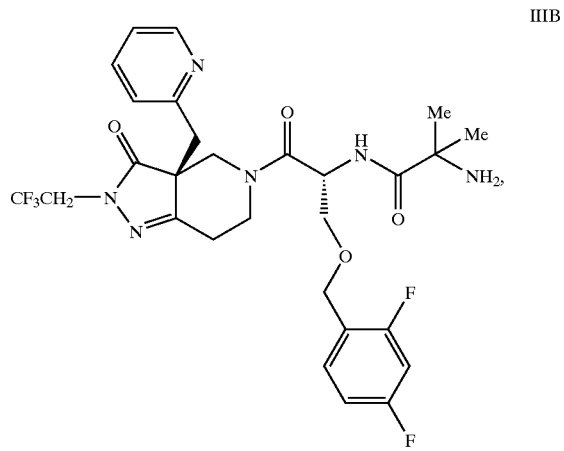

IIIB is prepared.

28. A process of claim 21 wherein said acid is trifluoroacetic acid.

29. A process of claim 28 wherein: R³ is phenylmethyloxymethyl or 2,4-difluorophenylmethyloxymethyl; in step b, said organic amine is triethylamine; and in step c, said coupling reagent is propane phosphonic acid anhydride.

30. A process of claim 29 wherein R¹ is methyl or 2,2,2-trifluoroethyl and R² is phenylmethyl or 2-pyridylmethyl.

31. A process of claim 30 wherein said compound of Formula III selected from 2-amino-N-[2-(3a(R)-benzyl-2-methyl-3-oxo-2,3,3a,4,6,7-hexahydro-pyrazolo-[4,3-c]pyridin-5-yl-1(R)-benzyloxylmethyl-2-oxo-ethyl]-isobutyramide and 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl-2-methyl-propionamide is prepared.

32. A process of claim 30 wherein a compound of formula IIIA,

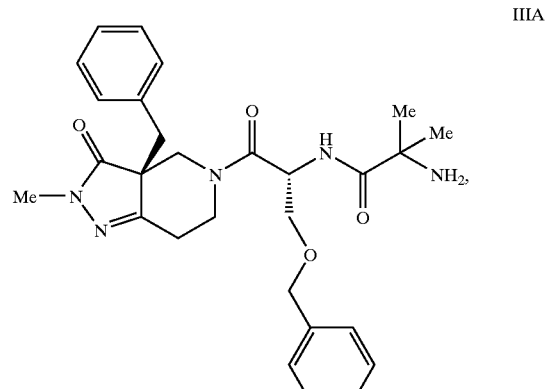

IIIA is prepared.

33. A process of claim 30 wherein a compound of formula IIIB,

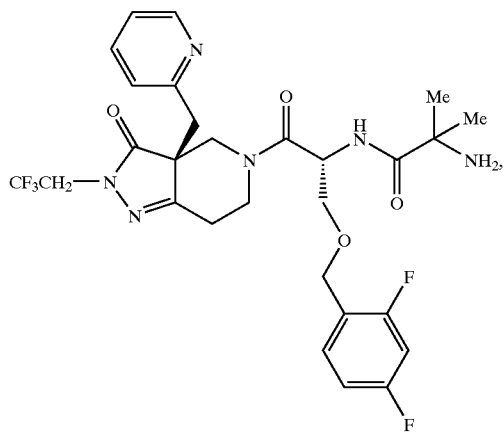

is prepared.

34. A process of claim 19 wherein said Prt is tert-butyloxycarbonyl and said tert-butyloxycarbonyl is removed by reacting said compound of Formula II with an acid.

35. A process of claim 34 wherein said acid is methanesulfonic acid.

36. A process of claim 35 wherein: $R^3$ is phenylmethyloxymethyl or 2,4-difluorophenylmethyloxymethyl; in step b, said organic amine is triethylamine; and in step f, said coupling reagent is propane phosphonic acid anhydride.

37. A process of claim 36 wherein $R^1$ is methyl or 2,2,2-trifluoroethyl and $R^2$ is phenylmethyl or 2-pyridylmethyl.

38. A process of claim 37 wherein said compound of Formula III selected from 2-amino-N-[2-(3a(R)-benzyl-2-methyl-3-oxo-2,3,3a,4,6,7-hexahydro-pyrazolo-[4,3-c]pyridin-5-yl)-1(R)-benzyloxylmethyl-2-oxo-ethyl]-isobutyramide and 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl-2-methyl-propionamide.

39. A process of claim 37 wherein a compound of formula IIIA,

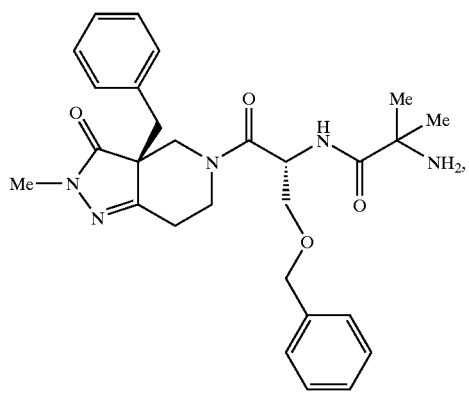

is prepared.

40. A process of claim 37 wherein a compound of formula IIIB, is prepared.

41. A process of claim 34 wherein said acid is trifluoroacetic acid.

42. A process of claim 41 wherein: $R^3$ is phenylmethyloxymethyl or 2,4-difluorophenylmethyloxymethyl; in step b, said organic amine is triethylamine; and in step f, said coupling reagent is propane phosphonic acid anhydride.

43. A process of claim 42 wherein $R^1$ is methyl or 2,2,2-trifluoroethyl and $R^2$ is phenylmethyl or 2-pyridylmethyl.

44. A process of claim 43 wherein said compound of Formula III selected from 2-amino-N-[2-(3a(R)-benzyl-2-methyl-3-oxo-2,3,3a,4,6,7-hexahydro-pyrazolo-[4,3-c]pyridin-5-yl-1(R)-benzyloxylmethyl-2-oxo-ethyl]-isobutyramide and 2-amino-N-(1(R)-(2,4-difluoro-benzyloxymethyl)-2-oxo-2-(3-oxo-3a(R)-pyridin-2-ylmethyl)-2-(2,2,2-trifluoro-ethyl)-2,3,3a,4,6,7-hexahydro-pyrazolo[4,3-c]pyridin-5-yl)-ethyl-2-methyl-propionamide.

45. A process of claim 43 wherein a compound of formula IIIA, is prepared.

46. A process of claim 43 wherein a compound of formula IIIB,

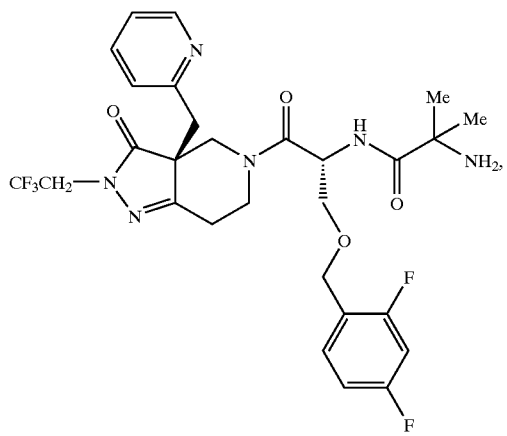

is prepared.

47. A polymorph of a dihydrate of a compound of formula XX:

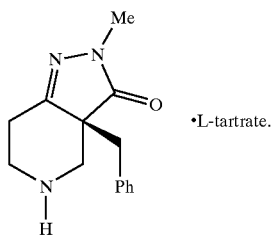

48. A polymorph of claim 47 having the X-Ray crystal structure according to FIG. 1.

49. A polymorph of claim 47 having the atomic coordinates and equivalent isotropic displacement coefficients as set forth in Table II:

TABLE II

Atomic coordinates (×10⁴) and equivalent isotropic displacement coefficients ($Å^2 \times 10^3$)

| | x | y | z | U(eq) |
|---|---|---|---|---|
| C(1') | 7050 (7) | 12045 (7) | 6424 (4) | 31(1) |
| O(1A') | 5715 (5) | 12748 (6) | 6097 (3) | 41(1) |
| O(1B') | 8234 (5) | 12946 (6) | 6748 (3) | 41(1) |
| C(2') | 7120 (6) | 9881 (7) | 6388 (4) | 29(1) |
| O(2') | 8733 (5) | 9232 (6) | 6715 (3) | 37(1) |
| C(3') | 6707 (7) | 9167 (7) | 5599 (4) | 32(1) |
| O(3') | 7899 (5) | 9726 (6) | 5160 (3) | 47(1) |
| C(4') | 6647 (7) | 6999 (7) | 5583 (4) | 32(1) |
| O(4A') | 5644 (5) | 6263 (6) | 5971 (3) | 39(1) |
| O(4B') | 7465 (5) | 6110 (7) | 5213 (3) | 59(1) |
| N(1) | 5011 (6) | 8379 | 1995 (3) | 43(1) |
| N(2) | 4317 (6) | 6558 (7) | 1896 (3) | 40(1) |
| C(2A) | 2623 (6) | 6380 (8) | 1541 (4) | 55(1) |
| C(3) | 5357 (7) | 5149 (8) | 2171 (4) | 36(1) |
| O(3) | 5039 (5) | 3491 (6) | 2188 (3) | 46(1) |
| C(4) | 6998 (6) | 6172 (8) | 2450 (3) | 28(1) |
| C(5) | 6515 (6) | 8177 (8) | 2299 (4) | 33(1) |
| C(6) | 7511 (6) | 5878 (8) | 3290 (4) | 39(1) |
| N(7) | 8723 (6) | 7355 (7) | 3591 (3) | 40(1) |
| C(8) | 8153 (7) | 9366 (8) | 3440 (4) | 49(1) |
| C(9) | 7643 (7) | 9700 (8) | 2603 (4) | 46(1) |
| C(10) | 8290 (6) | 5440 (8) | 1989 (4) | 37(1) |

TABLE II-continued

Atomic coordinates (×10⁴) and equivalent isotropic displacement coefficients ($Å^2 \times 10^3$)

| | x | y | z | U(eq) |
|---|---|---|---|---|
| C(11) | 7862 (7) | 5776 (8) | 11667 (4) | 43(1) |
| C(12) | 8463 (7) | 7317 (8) | 853 (4) | 69(1) |
| C(13) | 8108 (8) | 7675 (9) | 76 (5) | 97(1) |
| C(14) | 7080 (*) | 6405 (9) | −336 (5) | 96(1) |
| C(15) | 6443 (8) | 4882 (8) | −59 (5) | 81(1) |
| C(16) | 6872 (7) | 4533 (8) | 705 (4) | 75(1) |
| O(1W) | 8100 (5) | 6278 (7) | 7609 (3) | 54(1) |
| O(2W) | 10828 (5) | 8138 (7) | 5099 (3) | 62(1) |

50. A polymorph of claim 49 further having the bond lengths as set forth in Table III:

TABLE III

Bond Lengths (Å)

| C(1')–O(1A') | 1.262(7) | C(1')–O(1B') | 1.229 (7) |
|---|---|---|---|
| (C1')–C(2') | 1.525(7) | C(2')–O(2') | 1.4347 (6) |
| C(2')–C(3') | 1.500(9) | C(3')–O(3') | 1.416 (8) |
| C(3')–C(4') | 1.526(7) | C(4')–O(4A') | 1.277 (8) |
| C(4')–O(4B') | 1.201(8) | N(1)–N(2) | 1.402 (5) |
| N(1)–C(5) | 1.278(7) | N(2)–C(2A) | 1.443 (7) |
| N(2)–C(3) | 1.350(7) | C(3)–O(3) | 1.196 (7) |
| C(3)–C(4) | 1.541(7) | C(4)–C(5) | 1.478 (7) |
| C(4)–C(6) | 1.526(9) | C(4)–C(10) | 1.544 (9) |
| C(5)–C(9) | 1.465(7) | C(6)–N(7) | 1.481 (7) |
| N(7)–C(8) | 1.501(7) | C(8)–C(9) | 1.524 (10) |
| C(10)–C(11) | 1.492(9) | C(11)–C(12) | 1.355 (9) |
| C(11)–C(16) | 1.380(8) | C(12)–C(13) | 1.411 (12) |
| C(13)–C(14) | 1.365(9) | C(14)–C(15) | 1.327 (10) |
| C(15)–C(16) | 1.393(11) | | |

51. A polymorph of claim 50 further having the bond angles as set forth in Table IV:

TABLE IV

Bond Angles (°)

| O(1A')–C(1')–O(1B') | 125.8(5) | O(1A')–C(1')–C(2') | 114.1(5) |
|---|---|---|---|
| O(1B')–C(1')–C(2') | 120.2(5) | C(1')–C(2')–O(2') | 109.8(4) |
| C(1')–C(2')–C(3') | 111.7(5) | O(2')–C(2')–C(3') | 109.7(5) |
| C(2')–C(3')–O(3') | 111.9(4) | C(2')–C(3')–C(4') | 110.7(5) |
| O(3')–C(3')–C(4') | 106.9(5) | C(3')–C(4')–O(4A') | 114.6(5) |
| C(3')–C(4')–O(4B') | 120.7(6) | O(4A')–C(4')–O(4B') | 124.6(5) |
| N(2)–N(1)–C(5) | 107.4(3) | N(1)–N(2)–C(2A) | 118.7(4) |
| N(1)–N(2)–C(3) | 113.8(4) | C(2A)–N(2)–C(3) | 127.5(5) |
| N(2)–C(3)–O(3) | 126.6(5) | N(2)–C(3)–C(4) | 104.3(4) |
| O(3)–C(3)–C(4) | 129.0(5) | C(3)–C(4)–C(5) | 100.9(4) |
| C(3)–C(4)–C(6) | 110.4(5) | C(5)–C(4)–C(6) | 109.6(5) |
| C(3)–C(4)–C(10) | 108.2(5) | C(5)–C(4)–C(10) | 114.0(5) |
| C(6)–C(4)–C(10) | 113.0(5) | N(1)–C(5)–C(4) | 113.4(4) |
| N(1)–C(5)–C(9) | 126.2(4) | C(4)–C(5)–C(9) | 119.5(4) |
| C(4)–C(6)–N(7) | 109.4(5) | C(6)–N(7)–C(8) | 115.0(4) |
| N(7)–C(8)–C(9) | 110.7(5) | C(5)–C(9)–C(8) | 108.4(5) |
| C(4)–C(10)–C(11) | 114.5(4) | C(10)–C(11)–C(12) | 120.2(5) |
| C(10)–C(11)–C(16) | 121.6(6) | C(12)–C(11)–C(16) | 118.3(7) |
| C(11)–C(12)–C(13) | 122.0(6) | C(12)–C(13)–C(14) | 115.9(7) |
| C(13)–C(14)–C(15) | 124.7(8) | C(14)–C(15)–C(16) | 117.8(6) |
| C(11)–C(16)–C(15) | 121.2(6) | | |

52. A polymorph of claim 51 further having the anisotropic displacement coefficients as set forth in Table V:

TABLE V

Anisotropic displacement coefficients ($Å^2 \times 10^3$)

| | $U_{11}$ | $U_{22}$ | $U_{33}$ | $U_{12}$ | $U_{13}$ | $U_{23}$ |
|---|---|---|---|---|---|---|
| C(1') | 32 (1) | 26 (1) | 34(1) | 2 (1) | 5 (1) | −8 (1) |
| O(1A') | 35 (1) | 19 (1) | 67(1) | −4 (1) | 2 (1) | 2 (1) |
| O(1B') | 35 (1) | 26 (1) | 60(1) | −4 (1) | −2 (1) | −13 (1) |
| C(2') | 32 (1) | 17 (1) | 36(1) | 1 (1) | −1 (1) | 1 (1) |
| O(2') | 32 (1) | 33 (1) | 43(1) | 4 (1) | −1 (1) | 0 (1) |
| C(3') | 41 (1) | 18 (1) | 37(1) | 6 (1) | 6 (1) | −6 (1) |
| O(3') | 71 (1) | 33 (1) | 41(1) | −2 (1) | 23 (1) | 1 (1) |
| C(4') | 28 (1) | 27 (1) | 39(1) | 2 (1) | 3 (1) | 2 (1) |
| O(4A') | 41 (1) | 32 (1) | 45(1) | −7 (1) | 10 (1) | −9 (1) |
| O(4B') | 56 (1) | 35 (1) | 92(1) | 7 (1) | 32 (1) | −2 (1) |
| N(1) | 39 (1) | 48 (1) | 37(1) | 4 (1) | −6 (1) | 7 (1) |
| N(2) | 30 (1) | 39 (1) | 47(1) | 2 (1) | −2 (1) | −4 (1) |
| C(2A) | 27 (1) | 66 (1) | 68(1) | −3 (1) | −2 (1) | −1 (1) |
| C(3) | 39 (1) | 40 (1) | 30(1) | 8 (1) | 10 (1) | −7 (1) |
| O(3) | 45 (1) | 27 (1) | 65(1) | −3 (1) | 5 (1) | 1 (1) |
| C(4) | 23 (1) | 34 (1) | 26(1) | 0 (1) | 2 (1) | 3 (1) |
| C(5) | 31 (1) | 32 (1) | 36(1) | −1 (1) | 6 (1) | 0 (1) |
| C(6) | 38 (1) | 38 (1) | 38(1) | 4 (1) | 1 (1) | −4 (1) |
| N(7) | 39 (1) | 42 (1) | 34(1) | 1 (1) | −6 (1) | −1 (1) |
| C(8) | 44 (1) | 46 (1) | 54(1) | −1 (1) | 1 (1) | −9 (1) |
| C(9) | 41 (1) | 42 (1) | 52(1) | 6 (1) | 2 (1) | 0 (1) |
| C(10) | 37 (1) | 46 (1) | 29(1) | 6 (1) | 9 (1) | 4 (1) |
| C(11) | 39 (1) | 55 (1) | 37(1) | 10 (1) | 7 (1) | −2 (1) |
| C(12) | 72 (1) | 85 (1) | 49(1) | 4 (1) | 2 (1) | 1 (1) |
| C(13) | 103 (1) | 108 (1) | 82(1) | 2 (1) | 16 (1) | 27 (1) |
| C(14) | 103 (1) | 108 (1) | 73(1) | 13 (1) | 4 (1) | 6 (1) |
| C(15) | 81 (1) | 93 (1) | 63(1) | −4 (1) | −6 (1) | −17 (1) |
| C(16) | 80 (1) | 88 (1) | 58(1) | −4 (1) | 13 (1) | −12 (1) |
| O(1W) | 56 (1) | 45 (1) | 60(1) | −7 (1) | 7 (1) | −2 (1) |
| O(2W) | 58 (1) | 48 (1) | 91(1) | 3 (1) | 42 (1) | 7 (1) |

53. A polymorph of claim 52 further having the hydrogen atom coordinates and isotropic displacement coefficients as set forth in Table VI:

TABLE VI

H-Atom coordinates ($\times 10^4$) and isotropic displacement coefficients ($Å^2 \times 10^3$)

| | x | y | z | U |
|---|---|---|---|---|
| H(2') | 6314 | 9385 | 6665 | 80 |
| H(2A') | 8195 (10) | 8867 (10) | 7105 (9) | 50 |
| H(3') | 5656 | 9704 | 5398 | 80 |
| H(3A') | 8259 (10) | 11720 (10) | 5037 (9) | 50 |
| H(4A') | 5234 (10) | 6488 (10) | 6270 (9) | 50 |
| H(2A) | 2319 | 5061 | 1512 | 80 |
| H(2B) | 2495 | 6907 | 1046 | 80 |
| H(2C) | 1928 | 7053 | 1829 | 80 |
| H(6A) | 7999 | 4642 | 3381 | 80 |
| H(6B) | 6562 | 5972 | 3533 | 80 |
| H(7A) | 9771 (10) | 7980 (10) | 3431 (9) | 50 |
| H(7B) | 9183 (10) | 7721 (10) | 4160 (9) | 50 |
| H(8A) | 7229 | 9605 | 3689 | 80 |
| H(8B) | 9033 | 10220 | 3630 | 80 |
| H(9A) | 8599 | 9685 | 2362 | 80 |
| H(9B) | 7101 | 10908 | 2520 | 80 |
| H(10A) | 8417 | 4095 | 2071 | 80 |
| H(10B) | 9315 | 6067 | 2166 | 80 |
| H(12) | 9152 | 8192 | 1169 | 80 |
| H(13) | 8559 | 8747 | −149 | 80 |
| H(14) | 6799 | 6628 | −864 | 80 |
| H(15) | 5710 | 4049 | −375 | 80 |
| H(16) | 6471 | 3406 | 915 | 80 |
| H(1WA) | 8471 (10) | 5946 (10) | 7323 (9) | 52(1) |
| H(1WB) | 6863 (10) | 5969 (10) | 7529 (9) | 50 |
| H(2WA) | 11347 (10) | 8095 (10) | 5456 (9) | 50 |
| H(2WB) | 11515 (10) | 9176 (10) | 4829 (9) | 50 |

* * * * *

UNITED STATES PATENT AND TRADEMARK OFFICE

(12)     CERTIFICATE EXTENDING PATENT TERM
              UNDER 35 U.S.C. § 156

| | | | |
|---|---|---|---|
| (68) | PATENT NO. | : | 6,673,929 |
| (45) | ISSUED | : | January 6, 2004 |
| (75) | INVENTOR | : | Busch et al. |
| (73) | PATENT OWNER | : | RaQualia Pharma Inc. |
| (95) | PRODUCT | : | ENTYCE® (capromorelin oral solution) |

This is to certify that an application under 35 U.S.C. § 156 has been filed in the United States Patent and Trademark Office, requesting extension of the term of U.S. Patent No. 6,673,929 based upon the regulatory review of the product ENTYCE® (capromorelin oral solution) by the Food and Drug Administration. According to United States Patent and Trademark Office records, the original expiration date of the patent as of the date of issuance of this certificate was February 13, 2020. Because it appears that the requirements of the law have been met, this certificate extends the term of the patent for the period of

(94)                    851 days subject to the payment of maintenance fees as provided by law, with all rights pertaining thereto as provided by 35 U.S.C. § 156.

I have caused the seal of the United States Patent and Trademark Office to be affixed this 19th day of August 2020.

Andrei Iancu
Under Secretary of Commerce for Intellectual Property and
   Director of the United States Patent and Trademark Office